(12) United States Patent
Francis et al.

(10) Patent No.: US 10,220,116 B2
(45) Date of Patent: Mar. 5, 2019

(54) LIQUEFACTION OF BONE MATRIX

(71) Applicant: LifeNet Health, Virginia Beach, VA (US)

(72) Inventors: Michael Francis, Norfolk, VA (US); Roy Ogle, Norfolk, VA (US)

(73) Assignee: Lifenet Health, Virginia Beach, VA (US)

( * ) Notice: Subject to any disclaimer, the term of this patent is extended or adjusted under 35 U.S.C. 154(b) by 0 days.

(21) Appl. No.: 15/678,176

(22) Filed: Aug. 16, 2017

(65) Prior Publication Data

US 2017/0368227 A1 Dec. 28, 2017

Related U.S. Application Data

(62) Division of application No. 15/138,384, filed on Apr. 26, 2016, now Pat. No. 9,775,931, which is a division of application No. 14/377,272, filed as application No. PCT/US2013/025226 on Feb. 7, 2013, now Pat. No. 9,345,810.

(60) Provisional application No. 61/596,027, filed on Feb. 7, 2012.

(51) Int. Cl.
| | |
|---|---|
| A61L 27/36 | (2006.01) |
| C12N 5/077 | (2010.01) |
| A61K 35/28 | (2015.01) |
| A61L 27/38 | (2006.01) |
| A61L 27/54 | (2006.01) |
| C12N 5/00 | (2006.01) |
| A61K 35/32 | (2015.01) |
| A61K 38/18 | (2006.01) |
| C12N 5/0775 | (2010.01) |
| A61L 27/28 | (2006.01) |

(52) U.S. Cl.
CPC .......... *A61L 27/3687* (2013.01); *A61K 35/28* (2013.01); *A61K 35/32* (2013.01); *A61K 38/1875* (2013.01); *A61L 27/28* (2013.01); *A61L 27/3608* (2013.01); *A61L 27/3821* (2013.01); *A61L 27/3847* (2013.01); *A61L 27/54* (2013.01); *C12N 5/0068* (2013.01); *C12N 5/0654* (2013.01); *C12N 5/0662* (2013.01); *A61F 2210/00* (2013.01); *A61L 2300/414* (2013.01); *A61L 2400/12* (2013.01); *A61L 2430/02* (2013.01); *C12N 2501/155* (2013.01); *C12N 2506/1346* (2013.01); *C12N 2533/30* (2013.01); *C12N 2533/90* (2013.01)

(58) Field of Classification Search
CPC .......... A61L 27/3608; A61L 2300/414; A61L 2400/12; A61L 27/3687; A61L 27/3821; A61L 27/3847; A61L 27/54; A61L 2430/02; A61K 35/28; A61K 35/32; A61K 38/1875; C12N 2533/30; C12N 2533/90; C12N 5/006

USPC .............. 264/299; 424/422, 549; 427/2.26; 435/377, 402; 623/16.11, 23.58
See application file for complete search history.

(56) References Cited

U.S. PATENT DOCUMENTS

| | | | |
|---|---|---|---|
| 6,189,537 B1 | 2/2001 | Wolfinbarger | |
| 6,305,379 B1 | 10/2001 | Wolfinbarger | |
| 6,340,477 B1 * | 1/2002 | Anderson | A61K 35/32 424/422 |
| 9,849,214 B2 * | 12/2017 | Woodell-May | A61L 27/3608 |
| 2006/0257377 A1 * | 11/2006 | Atala | A61K 38/18 424/93.7 |
| 2010/0120115 A1 | 5/2010 | Ogle et al. | |
| 2011/0218646 A1 | 9/2011 | Pertici | |

FOREIGN PATENT DOCUMENTS

| | | |
|---|---|---|
| WO | 2009082554 A2 | 7/2009 |
| WO | 2010016942 A1 | 2/2010 |

OTHER PUBLICATIONS

Non-Final Office Action for Application No. 14/377,272, dated Aug. 17, 2015—7 pages.
Notice of Allowance for U.S. Appl. No. 14/377,272, dated Jan. 20, 2016—9 pages.
Anderson et al., "Biodegradation and Biocompatibility of PLA and PLGA Microspheres," Advanced Drug Delivery Review, vol. 28, 1997, pp. 5-24.
Ayres et al., "Measuring Fiber Alignment in Electrospun Scaffolds: A User's Guide to the 2D Fast Fourier Transform Approach," Journal of Biomaterials Science, Polymer Edition, vol. 19, No. 5, 2008, pp. 603-621.
Cleek et al., "Microparticles of Poly(DL-lactic-co-glycolic acid)/poly(ethylene glycol) Blends fro Controlled Drug Delivery," Journal of Controlled Release, vol. 48, 1997, pp. 259-268.
Fields et al., "Solid-Phase Synthesis and Stability of Triple-Helical Peptides Incorporating Native Collagen Sequences," Biopolymers, vol. 33, No. 11, 1993, pp. 1695-1707.
Guantieri et al., "Synthesis of Polypeptide Models of Collagen," Int. J. Peptide Protein Res., vol. 24, 1984, pp. 274-278.

(Continued)

*Primary Examiner* — Janet L Epps-Smith

(74) *Attorney, Agent, or Firm* — RatnerPrestia

(57) ABSTRACT

The invention relates to methods of preparing a bone matrix solution, a bone matrix implant, and variants thereof. The invention also relates to methods of cell culture using the same. The invention further relates to bone matrix scaffolds comprising one or more bone matrix nanofibers, methods of preparing, and methods of use thereof. The invention also relates to methods of culturing cells and promoting differentiation of stem cells using the same.

7 Claims, 11 Drawing Sheets

(56) References Cited

OTHER PUBLICATIONS

Lu et al., "Polymeric Delivery Vehicles for Bone Growth Factors," Park & Mrsny; Controlled Drug Delivery, ACS Symposium Series; American Chemical Society, 2000, pp. 124-138.
Pietrzak et al., "Assay of Bone Morphogenetic Protein-2, -4 and -7 in Human Demineralized Bone Matrix," Journal of Craniofacial Surgery, vol. 17, No. 1, 2006, pp. 84-90.
Schnaper et al., "Regulation of Cell Function by Extracellular Matrix," Pediatric Nephrology, vol. 7, 1993, pp. 96-104.
Zeugoils et al., "Electro-spinning of Pure Collagen Nano-fibres—Just an Expensive Way to Make Gelatin," Biomaterials, 20, 2008, pp. 2293-2305.
Behravesh et al., "Synthetic Biodegradable Polymers for Orthoaedic Applications," Clinical Orthopaedics and Related Research, No. 367S, 1999, pp. S118-S125.
Non Final Office Action for U.S. Appl. No. 15/138,384, dated Nov. 3, 2016, 13 pages.
Notice of Allowance for U.S. Appl. No. 15/138,384, dated Jul. 13, 2017, 5 pages.
Entire patent prosecution history of U.S. Appl. No. 14/377,272, filed Aug. 7, 2014, entitled, Liquefaction of Bone Matrix, now U.S. Pat. No. 9,345,810, issued May 24, 2016.
Entire patent prosecution history of U.S. Appl. No. 15/138,384, filed Apr. 26, 2016, entitled, "Liquefaction of Bone Matrix," now U.S. Pat. No. 9,775,931, issued Oct. 3, 2017.
Canadian Office Action for Canadian Application No. 2,863,967, dated Oct. 9, 2018, 4 pages.

* cited by examiner

LIQUEFACTION OF BONE MATRIX

CROSS-REFERENCE TO RELATED APPLICATIONS

This application is a divisional application of U.S. application Ser. No. 15/138,384, which is a divisional application of U.S. application Ser. No. 14/377,272, now U.S. Pat. No. 9,345,810, which claims priority to PCT International Application No. PCT/US2013/025226, filed Feb. 7, 2013, which claims priority to U.S. Provisional Application No. 61/596,027, the content of such applications being incorporated by reference herein in their entirety.

BACKGROUND OF THE INVENTION

The invention relates to methods of preparing a bone matrix solution, a bone matrix implant, and variants thereof. The invention also relates to methods of cell culture using the same.

The invention further relates to bone matrix scaffolds comprising one or more bone matrix nanofibers, methods of preparing, and methods of use thereof. The invention also relates to methods of culturing cells and promoting differentiation of stem cells using the same.

SUMMARY

The invention relates to methods of preparing a bone matrix solution comprising dissolving bone in an amount of an anhydrous solvent comprising (i) hexafluoroisopropanol (HFP) or 2, 2, 2-trifluoroethanol (TFE) and (ii) at least about 5 wt % trifluoroacetic acid (TFA) sufficient to form the bone matrix solution.

The invention also relates to methods of preparing a bone matrix implant with a predetermined shape comprising: dissolving a bone in an amount of an anhydrous solvent comprising (i) hexafluoroisopropanol (HFP) or 2, 2, 2-trifluoroethanol (TFE) and (ii) at least about 5 wt % trifluoroacetic acid (TFA) sufficient to form the bone matrix solution; exposing the bone solution to conditions sufficient to evaporate an amount of the solvent to form a colloidal gel; and allowing the colloidal gel to harden into the predetermined shape to form the bone matrix implant.

The invention also relates to methods of preparing a film of bone matrix on a surface comprising: dissolving a bone preparation in an amount of an anhydrous solvent comprising (i) hexafluoroisopropanol (HFP) or 2, 2, 2-trifluoroethanol (TFE), and (ii) at least about 5 wt % trifluoroacetic acid (TFA) sufficient to form the bone matrix solution; exposing the bone solution to conditions sufficient to evaporate an amount of the solvent to form a colloidal gel; coating the surface with the colloidal gel; and exposing the coated surface to conditions sufficient to further evaporate an amount of solvent to form a film. In particular, the bone may be demineralized bone or non-demineralized bone.

The invention also relates to methods of promoting osteogenesis, chondrogenic, or ligament/tendon differentiation of cells, comprising contacting the cells on a surface coated with the bone matrix produced by the method described herein.

The invention further relates to bone matrix scaffolds comprising one or more bone matrix nanofibers.

The invention also relates to methods of preparing the bone matrix scaffold, the method comprising dissolving bone in an amount of an anhydrous solvent comprising (i) hexafluoroisopropanol (HFP) or 2, 2, 2-trifluoroethanol (TFE) and (ii) at least about 5 wt % trifluoroacetic acid (TFA) sufficient to form a bone matrix solution at a temperature between about 0° C. and about 22° C., and electrospinning the bone matrix solution to form the bone matrix scaffold.

The invention also relates to methods of preparing the bone matrix scaffold, the method comprising dissolving bone in an amount of an anhydrous solvent comprising (i) hexafluoroisopropanol (HFP) or 2, 2, 2-trifluoroethanol (TFE) and (ii) at least about 5 wt % trifluoroacetic acid (TFA) sufficient to form a bone matrix solution at a temperature between about 0° C. and about 22° C., and neutralizing the bone matrix solution to form the bone matrix scaffold.

The invention also relates to bone matrix implants produced by the methods of preparing the bone matrix scaffold.

The invention further relates to methods of cell culture comprising culturing cells on the bone matrix scaffold in condition suitable for the cell culture. The invention also relates to methods of promoting differentiation of stem cells into osteoblasts, chondrocytes, ligament or tendon, the method comprising culturing the cells on the bone matrix scaffold in conditions suitable for the cell differentiation.

Significantly more cells are seen to attach to electrospun DBM as cross-linked with EDC or as blended with PCL as compared to cell left to attach on glass coverslips alone in a cell attachment assay. Cell were grown in serum-free media over the course of 15, 30, 60 and 120 minutes with cell counts of crystal violet stained cells that were quantitated with image J, and verified by optical densitometry of released stain (not shown). The DBM film dissolved rapidly and negatively biased the attachment assay at all time points. Cell attachment was shown to be statistically significantly higher on DBM-EDC, DBM/PCL and PCL relative to attachment on the coverslip alone with cells grown in serum free media as determined by a one-way ANOVA ($P<0.05$).

Figure 9:
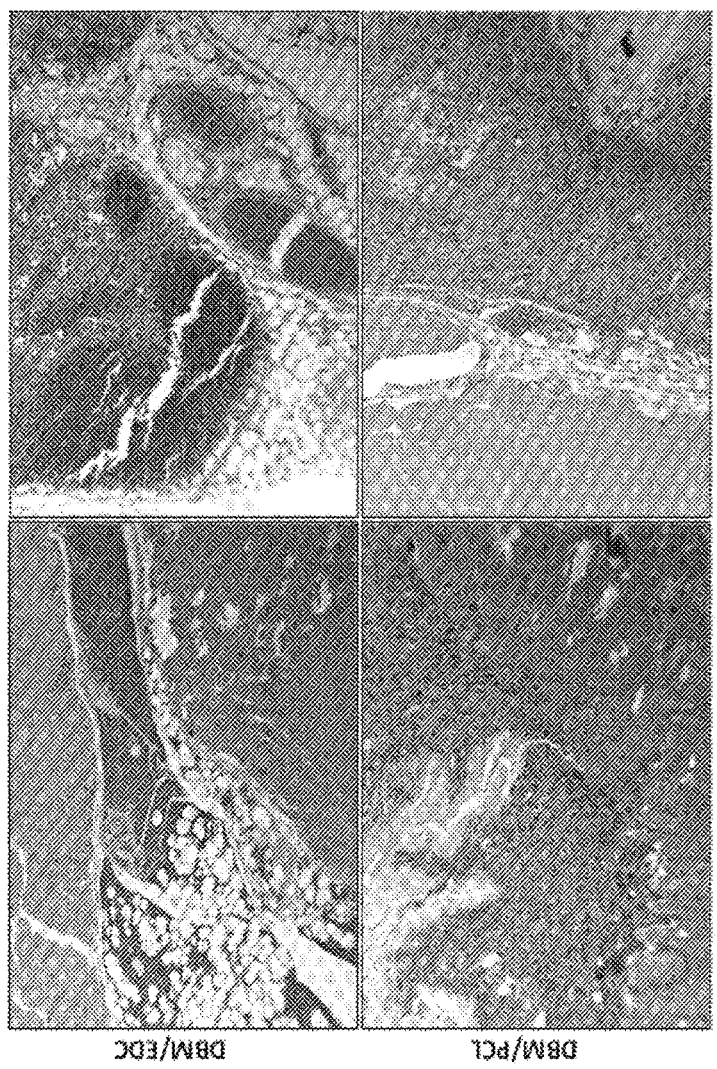

FIG. 9 depicts in vivo implants of bone matrix scaffolds. A four-week animal study with implanted EDC cross-linked DBM and DBM/PCL scaffolds was performed using 0.1 cc of material implanted into a rat intramuscularmuscle pouch assay. H&E stained sections of implanted electrospun DBM constructs indicate minimal immunoreactivity and high cell recruitment and infiltration into electrospun materials. Abundant, dense, loosely-organized layers of mesenchymal-like-cells are seen throughout the electrospun constructs, with a high degree of original scaffold turnover observed, particularly in DBM/PCL sample. Adipogenic differentiation is potentially seen in DBM/EDC samples, with unique interdigitations observed in most DBM/PCL samples at the scaffold/muscle boundary, evocative of a tendon-type structural interface forming.

Figure 10:
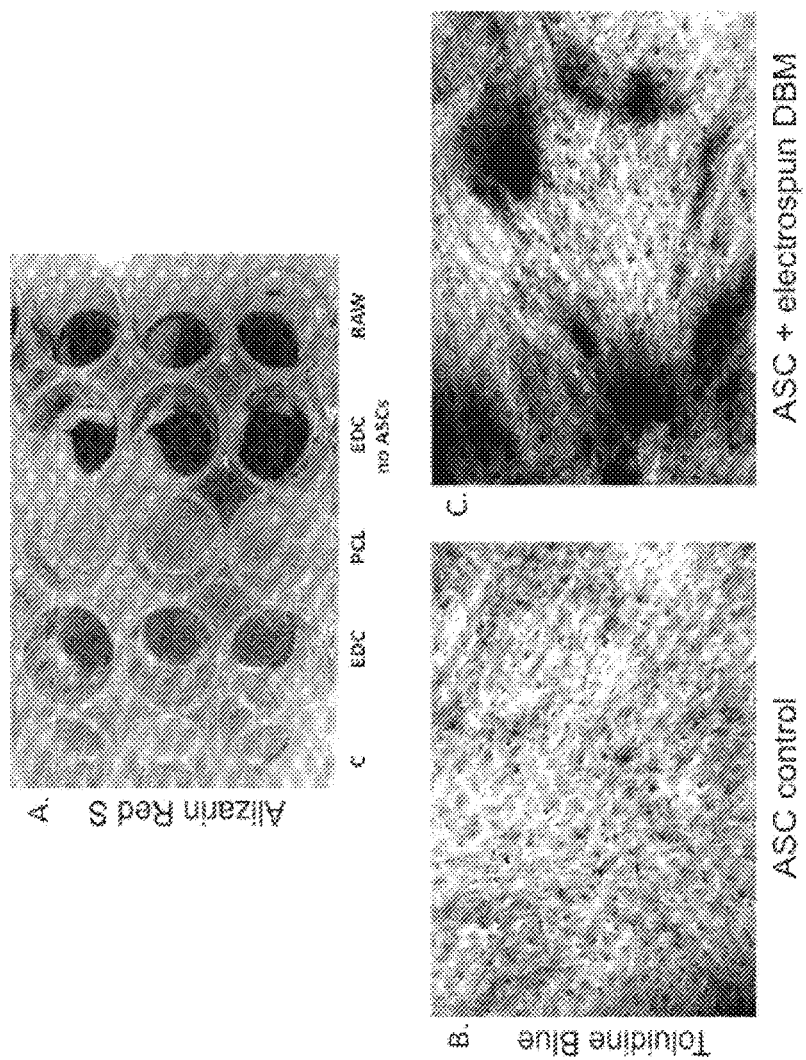

FIG. 10 depicts Alizarin Red S and Toluidine Blue Assay of bone matrix scaffolds. Alizarin red S histology stains confirmed the presence of calcium in adipose stem cell seeded electrospun DBM crosslinked with EDC (A-EDC), with DBM/PCL (A-PCL), with DBM/EDC without cells (A-EDC no ASCs) and of the unprocessed DBM granules (A-RAW) (A). Toluidine blue suggests the formation of new bone from ASCs that are grown in the presence of electrospun DBM (C) vs grown in control ASC media for 3 weeks (B).

Figure 11:
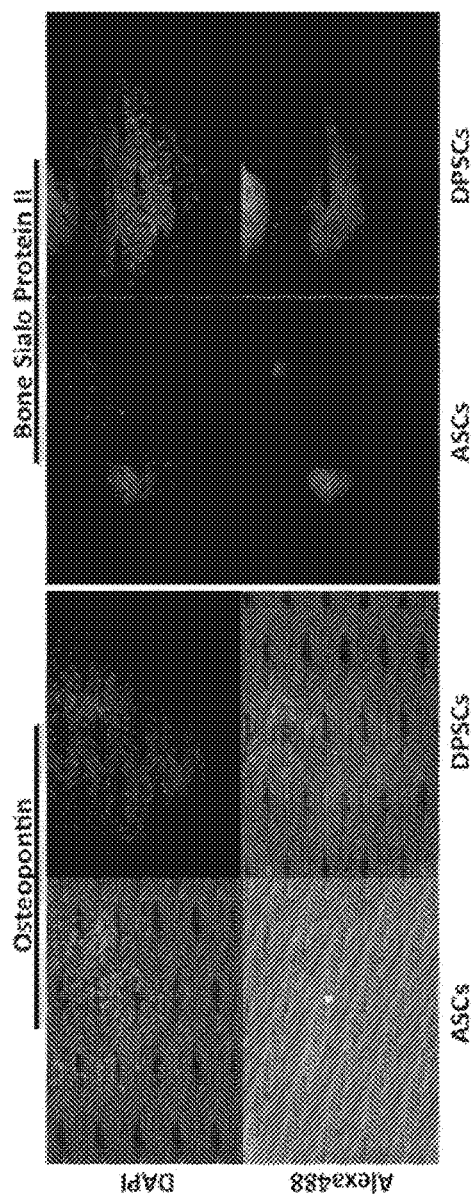

FIG. 11 depicts osteoinduction capability of bone matrix scaffolds. Uncrosslinked electrospun DBM was cultured with adipose derived stem cells (ASCs) and dental pulp stem cells (DPSCs) to assay the osteoinductive potential of this material. Both ASCs and DPSCs showed expression of alexa488 labeled bone sialo protein I (aka osteopontin) and bone sialo protein II, as seen in the many cell mounds or nodules that formed throughout the cultures. Cell nuclei are shown counter-labeled with DAPI.

DETAILED DESCRIPTION OF THE INVENTION

The invention relates to methods of preparing a bone matrix solution. The method of preparing a bone matrix solution according to some embodiments of the present invention comprises dissolving bone in an anhydrous solvent. The bone includes, but is not limited to, autograft bone, allograft bone, and xenograft bone. Such bone includes any bone from any source, including, but not limited to, bone from a living human donor, bone from a human cadaveric donor, and bone from an animal. The bone may include cortical bone and/or cancellous bone and/or cortico-cancellous bone.

The bone may be demineralized bone or non-demineralized bone. "Demineralized bone matrix (DBM)" as used herein refers to bone having less than about 8 wt % residual calcium. Demineralization involves treating a bone tissue to remove its inorganic mineral hydroxyapatite material. The level of demineralization of a bone tissue is defined by the amount (wt %) of residual calcium found in the demineralized bone. In some embodiments, the demineralized bone may still contain physiologically active levels of growth and differentiation factors (e.g., osteogenic growth factors, such as bone morphogenetic proteins (BMPs)) remaining from the initial bone even after the demineralization treatment. In further embodiments, the demineralized bone may contain collagen, glycosaminoglycans, osteocalcin, osteonectin, bone sialo protein, osteopontin, and mixtures thereof. "Non-demineralized bone" as used in the present application refers to bone that has not been treated to remove minerals present such as, for example, hydroxyapatite.

The extracellular matrix of bone is comprised primarily of collagen type I and inorganic bone mineral hydroxyapatite $(Ca_{10}(PO_4)_6(OH)_2)$. "Collagen type I" refers to a heterotrimer of two alpha1(I) and one alpha2(I) chains, which is the most common form of fibrillar collagen in a body. Collagen type I is present in the form of elongated fibers greater than 500 μm in length and 500 nm in diameter. These building blocks of the collagen are rod-like triple helices that are stabilized by intramolecular hydrogen bonds between Gly and Hyp in adjacent chains. Dissolving the collagen type I in a solvent and maintaining its native biological activities, however, has been challenging because its native conformation can be degraded by a disruption in the intermolecular crosslinks of the aldimine or keto-imine type and/or a disruption in the intramolecular bonds of the triple helical structure. For example, dilute acidic solvents have been used to dissolve collagen by breaking the intermolecular crosslinks of its aldimine type, while proteolytic enzymes, such as pepsin, have been used to cleave the more stable crosslinks of its keto-imine type. Moreover, dissolving and electro-spinning collagen in fluoroalcohol solvents, such as 1, 1, 1, 3, 3, 3-hexafluoro-2-propanol (HFP) and 2, 2, 2-trifluoroethanol (TFE), have been shown to result in the significant disruption in the intramolecular bonds of the collagen triple helices (Zeugolis et al., Biomaterials 29, 2008, 2293-2305). For the same reasons, it has been challenging to dissolve the extracellular matrix of bone comprised primarily of collagen type I in a solvent while maintaining its native biological activities.

Moreover, the extracellular matrix of bone is comprised of a complex mixture of the collagen type I, the inorganic bone mineral hydroxyapatite, other proteins (e.g. laminins, fibronectin, elastin, and growth factors), other minerals (e.g. calcium phosphate, magnesium, carbonate, and fluoride ions), and carbohydrates (e.g. parts of glycoproteins).

Accordingly, dissolving bone has been even more challenging in view of the complex mixture of the various components in the bone.

Fluoroalcohol solvents (e.g. HFP and TFE), have been shown to disrupt the intramolecular bonds of the collagen triple helices and thus were not considered as a desirable candidate for dissolving collagen type I. The present invention surprisingly shows that dissolving bone in an anhydrous solvent comprising a highly volatile fluoroalcohols (e.g. HFP, TFE, and their variants) and trifluoroacetic acid (TFA), would still maintain the native structure and/or triple collagen structure of the collagen type I in the bone. In some embodiments, collagen type I in the bone matrix solution prepared according to the methods described herein consists of collagen in its native structure or in its native triple helical structure. In other embodiments, collagen type I in the bone matrix solution prepared according to the methods described herein essentially consists of collagen in its native structure or its native triple helical structure. In additional embodiments, more than about 99%, 98%, 97%, 96%, 95%, 90%, 80%, 70%, 60%, 50%, 40%, 30%, 20%, 10%, 5%, 3% or 1% of collagen type I in the bone matrix solution prepared according to the methods described herein is collagen in its native structure or in its native triple helical structure. In yet additional embodiments, less than about 100%, 99%, 98%, 97%, 96%, 95%, 90%, 80%, 70%, 60%, 50%, 40%, 30%, 20%, 10%, 5%, or 3% collagen type I in the bone matrix solution prepared according to the methods described herein is collagen in its native structure. In further embodiments, between about 100% and about 95%, between about 100% and about 85%, between about 95% and about 85%, between about 85% and about 75%, between about 85% and about 65%, between about 75% and about 65%, between about 65% and about 45%, between about 65% and about 55%, between about 55% and about 35%, between about 55% and about 45%, between about 45% and about 25%, between about 45% and about 35%, between about 35% and about 15%, between about 35% and about 25%, between about 25% and about 5%, or between about 25% and about 15% of collagen type I in the bone matrix solution prepared according to the methods described herein is collagen in its native structure or in its native triple helical structure.

The solvents of the present invention may be anhydrous solvents or non-anhydrous solvents with a protectant. The protectant prevents heat or solvent related degradation or denaturation of proteins in the non-anhydrous solvents. The protectants include, but are not limited to, bovine serum albumin and human serum albumin, which has been shown to enhance the long term stability of proteins dissolved in organic solvents.

Anhydrous trifluoroacetic acid (TFA) has been used in the peptide synthesis to cleave an N-terminal amino acid of a purified synthetic peptide, such as polypeptide models of collagen (Guantieri and Tamburro, Int. J. Peptide Protein Res., 2, 1984, 274-278; Fields et al., Biopolymers, 33, 11, 1993, 1695-1707). The extracellular matrix of bone, however, is comprised of a complex mixture of carbohydrates, proteins, and minerals and thus is difficult to be dissolved in the same solution as the purified synthetic peptide. For example, as shown in the comparative examples herein, a solvent having 50% TFA and 50% dimethylformamide (DMF) was not able to dissolve the bone even after an extended period of stirring on the order of 14-28 days at 4° C. or 22° C. The present invention surprisingly shows an anhydrous solvent comprising TFA and a volatile fluoroalcohol (e.g. HFP, TFE, and their variants) effectively dissolves bone having complex mixtures of carbohydrates, proteins, and minerals. In some embodiments of the present invention, a secondary solvent may be added to the TFA and fluoroalcohol solvent. Specifically, the secondary solvent may be selected from the group consisting of the family of hexa-fluoro-isopropanol (HFP), N-methyl morpholine N-oxide, calcium nitrate-methanol, or related organic solvents.

The anhydrous solvent to dissolve the bone according to some embodiments of the present invention may comprise (i) hexafluoroisopropanol (HFP), 2, 2, 2-trifluoroethanol (TFE) or their variants, and (ii) trifluoroacetic acid (TFA). As used herein, the variants of HFP and TFE refers to other fluoroalcohol solvents, including, but not limited to, 2,3-difluorobenzyl alcohol, 1,3-difluoro-2-propanol, trifluoroethanol, 2,2,3,3,4,4,4-heptafluoro-1-butanol, 3,3,4,4,5,5,5-heptafluoro-2-pentanol, 2,2,3,3,4,4,5,5-octafluoro-1-pentanol, 1H,1H,2H,2H-perfluoro-1-decanol, 1H,1H,2H,3H,3H-perfluorononane-1,2-diol, 1H,1H,9H-perfluoro-1-nonanol, 1H,1H-perfluorooctanol, 1H,1H,2H,2H-perfluorooctanol, 1H, 1H, 2H, 3H, 3H-perfluoroundecane-1,2-diol, trifluorobutanol, 1,1,1-trifluoro-2-propanol, 3,3,3-trifluoro-1-propanol, 1,1,1,3,3,3-hexafluoro-2-propanol, 1,1,1,3,3,3-hexafluoro-2-methyl-2-propanol, 2,2,3,4,4,4-hexafluoro-1-butanol, 2-trifluoromethyl-2-propanol, 2,2,3,3-tetrafluoro-1-propanol, 3,3,3-trifluoro-1-propanol, 4,4,4-trifluoro-1-butanol, and a mixture thereof. In further embodiments, the anhydrous solvent to dissolve the bone may consist of (i) HFP, TFE or their variants, and (ii) trifluoroacetic acid (TFA). In additional embodiments, the anhydrous solvent to dissolve the bone may exclude dimethylformamide (DMF).

In one aspect, the amount of HFP, TFE, their variants in the solvent may be about 95 wt %, 90 wt %, 80 wt %, 70 wt %, 60 wt %, 50 wt %, 40 wt %, 30 wt %, 20 wt %, 10 wt %, 5 wt %, between about 95 wt % and about 5 wt %, between about 95 wt % and about 10 wt %, between about 95 wt % and about 25 wt %, between about 95 wt % and about 45 wt %, between about 95 wt % and about 65 wt %, between about 95 wt % and about 85 wt %, between about 95 wt % and about 90 wt %, between about 90 wt % and about 5 wt %, between about 90 wt % and about 10 wt %, between about 90 wt % and about 25 wt %, between about 90 wt % and about 45 wt %, between about 90 wt % and about 65 wt %, between about 90 wt % and about 85 wt %, between about 80 wt % and about 5 wt %, between about 80 wt % and about 10 wt %, between about 80 wt % and about 25 wt %, between about 80 wt % and about 45 wt %, between about 80 wt % and about 65 wt %, and between about 80 wt % and about 75 wt %. In another aspect, the amount of TFA in the solvent may be at least about 1, 2, 3, 4, or 5 wt %, 6 wt %, 7 wt %, 8 wt %, 9 wt %, 10 wt %, 13 wt %, 15 wt %, 20 wt %, 25 wt %, 30 wt %, 40 wt %, 50 wt %, 60 wt %, 70%, 80 wt %, or 90 wt % between about 95 wt % and about 5 wt %, between about 95 wt % and about 10 wt %, between about 95 wt % and about 25 wt %, between about 95 wt % and about 45 wt %, between about 95 wt % and about 65 wt %, between about 95 wt % and about 85 wt %, between about 95 wt % and about 90 wt %, between about 90 wt % and about 5 wt %, between about 90 wt % and about 10 wt %, between about 90 wt % and about 25 wt %, between about 90 wt % and about 45 wt %, between about 90 wt % and about 65 wt %, between about 90 wt % and about 85 wt %, between about 80 wt % and about 5 wt %, between about 80 wt % and about 10 wt %, between about 80 wt % and about 25 wt %, between about 80 wt % and about 45 wt %, between about 80 wt % and about 65 wt %, and between about 80 wt % and about 75 wt %.

As used herein, the term "about" modifying, for example, the quantity of an ingredient in a composition, concentrations, volumes, process temperature, process time, yields, flow rates, pressures, and like values, and ranges thereof, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities. The term "about" further may refer to a range of values that are similar to the stated reference value. In certain embodiments, the term "about" refers to a range of values that fall within 10, 9, 8, 7, 6, 5, 4, 3, 2, 1 percent or less of the stated reference value.

The amount of the anhydrous solvent used in preparing the bone matrix solution according to some embodiments of the present invention is the amount sufficient to dissolve the bone and thus sufficient to form the bone matrix solution at a temperature described as follows. In some aspects, the bone may be dissolved in the solvent described herein at about 37° C., 36° C., 35° C., 34° C., 33° C., 32° C., 31° C., 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C. or lower. In other aspects, the bone may be dissolved in the solvent described herein at a temperature lower than about 37° C., 36° C., 35° C., 34° C., 33° C., 32° C., 31° C., 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., or 4° C. In further aspects, the bone is dissolved in the solvent described herein at a temperature high enough to effectively break the bonds in a solid. In some embodiments, the bone may be dissolved in the solvent described herein at a temperature higher than about 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., 1° C., or 0° C. It has been found by the inventors that the temperature in which the bone is dissolved has an effect on the native structure and/or the native triple helical structure of collagen in the bone. In some embodiments, dissolving bone at temperatures below about room temperature, which is defined as 25° C., has provided an improved collagen product in its native structure and/or in its native triple helical structure compared to dissolving bone at higher temperatures. In some embodiments, bone is dissolved at a temperature below 22° C. In other embodiments, bone is dissolved at a temperature between about 4° C. and about 21° C.

The amount of the bone dissolved in the solvent according to some embodiments of the present invention may be between about 0.001 mg/mL and about 300 mg/mL, between about 1 mg/mL and about 300 mg/mL, between about 10 mg/mL and about 300 mg/mL, between about 20 mg/mL and about 300 mg/mL, between about 0.001 mg/mL and about 200 mg/mL, between about 1 mg/mL and about 320 mg/mL, between about 10 mg/mL and about 200 mg/mL, between about 20 mg/mL and about 200 mg/mL, between about 30 mg/mL and about 150 mg/mL, between about 50 mg/mL and about 150 mg/mL, between about 100 mg/mL and about 150 mg/mL, between about 130 mg/mL and about 150 mg/mL, between about 30 mg/mL and about 100 mg/mL, or between about 30 mg/mL and about 50 mg/mL. According to additional embodiments of the present invention, the bone may be dissolved by stirring the bone in the solvent described herein for more than about 3 hours, 6 hours, 12 hours, 24 hours, 36 hours, 48 hours, 3 days, 4 days, 5 days or 6 days. In another aspect, the bone may be dissolved by stirring the bone in the solvent described herein for less than about 5 hours, 10 hours, 15, hours, 20 hours, 25 hours, 30 hours, 40 hours, 50 hours, 4 days, 5 days, 6 days, 7 days, 8 days, 9 days, 10 days, 11 days, 12 days, 13 days, or 14 days. In another aspect, the bone may be dissolved by stirring the bone in the solvent described herein for about 3 hours, 5 hours, 6 hours, 10 hours, 12 hours, 15, hours, 20 hours, 24 hours, 25 hours, 30 hours, 40 hours, 50 hours, 4 days, 5 days, 6 days, 7 days, 8 days, 9 days, 10 days, 11 days, 12 days, 13 days, 14 days, 20 days, 30 days, 40 days, or 50 days. According to yet additional embodiments of the present invention, the bone to be dissolved in the solvent described herein may be in the forms of particles and/or powder. Demineralized bone particles may be prepared from cleaned and disinfected bone fragments that have been freeze-dried and ground/fractured into bone particles. Bone particles may be selected by, for example, using sieving devices (i.e., mesh sieves) commercially available to obtain particles within a desired size range. Such demineralized bone particles may have an average diameter of between about 125 microns and about 4 mm; between about 710 microns and about 2 mm; between about 125 microns and about 500 microns; between about 125 microns and about 850 microns; or between about 250 microns and about 710 microns. Certain embodiments of the present invention may include demineralized bone powder that is commercially available. For example, a suitable demineralized bone powder that is widely and reliably available is produced by LifeNet Health, Virginia Beach, Va.

The invention also relates to methods of preparing a bone matrix implant with a predetermined shape. An "implant" refers to any object that is designed to be placed partially or wholly within a patient's body for one or more therapeutic or prophylactic purposes such as for tissue augmentation, contouring, restoring physiological function, repairing or restoring tissues damaged by disease or trauma, and/or delivering therapeutic agents to normal, damaged or diseased organs and tissues. A "bone matrix implant" refers to a medical device or implant that includes a volume replacement material for augmentation or reconstruction to replace a whole or part of a bone structure. A predetermined shape of the bone matrix implant may be varied to fit the implant site. A "bone matrix" refers to any mixture of the volume replacement materials for augmentation or reconstruction to replace a whole or part of a bone structure.

The methods of preparing a bone matrix implant with a predetermined shape according to some embodiments of the present invention comprises dissolving a bone in an amount of an anhydrous solvent comprising (i) hexafluoroisopropanol (HFP), 2, 2, 2-trifluoroethanol (TFE) or isopropanol and (ii) at least about 5 wt % trifluoroacetic acid (TFA) sufficient to form a bone matrix solution; exposing the bone matrix solution to conditions sufficient to evaporate an amount of the solvent to form a colloidal gel; and allowing the colloidal gel to harden into the predetermined shape to form the bone matrix implant. In some embodiments, the colloidal gel may be placed in a mold to form the predetermined shape, formed with or without particles of bone in the suspension. As used herein, a "colloidal gel" refers to a colloid that has developed resistance to flow and thus is in a more solid form than a solution. A "colloid" refers to a system composed of a continuous medium throughout which are distributed small particles, e.g., 1 to 1000 nm in size or larger, that do not settle out under the influence of gravity; the particles may be in emulsion or in suspension. The invention further relates to a bone matrix implant produced by the method described herein.

Methods to evaporate the solvent to form a colloidal gel from the bone matrix solution according to some embodiments of the present invention may include, but are not limited to, air drying, vacuum drying, heat drying, and freeze drying. The amount of the solvent to form a colloidal gel from the bone matrix solution according to some embodiments of the present invention may be about 98 wt %, 95 wt %, 90 wt %, 85 wt %, 80 wt %, 75 wt %, 70 wt %, 65 wt %, 60 wt %, 55 wt %, 50 wt %, 45 wt %, 40 wt %, 35 wt %, 30 wt %, 25 wt %, 20 wt %, 15 wt %, 10 wt %, 5 wt %, or 0 wt %. In one aspect, the amount of the solvent to form a colloidal gel from the bone matrix solution may be less than about 98 wt %, 95 wt %, 90 wt %, 85 wt %, 80 wt %, 75 wt %, 70 wt %, 65 wt %, 60 wt %, 55 wt %, 50 wt %, 45 wt %, 40 wt %, 35 wt %, 30 wt %, 25 wt %, 20 wt %, 15 wt %, 10 wt %, or 5 wt %. In another aspect, the amount of the solvent to form a colloidal gel from the bone matrix solution may be more than about 98 wt %, 95 wt %, 90 wt %, 85 wt %, 80 wt %, 75 wt %, 70 wt %, 65 wt %, 60 wt %, 55 wt %, 50 wt %, 45 wt %, 40 wt %, 35 wt %, 30 wt %, 25 wt %, 20 wt %, 15 wt %, 10 wt %, 5 wt %, or 0 wt %.

The methods of preparing a bone matrix implant with a predetermined shape according to some embodiments of the present invention may further comprise adding a bioactive factor to the bone matrix solution described herein. A "bioactive factor" refers to protein, carbohydrate, or mineral that has any effect on a cellular activity. Examples of bioactive factors include, but are not limited to, an osteogenic growth factor, collagen, glycosaminoglycans, osteonectin, bone sialo protein, an osteoinductive factor, a chondrogenic factor, a cytokine, a mitogenic factor, a chemotactic factor, a transforming growth factor (TGF), a fibroblast growth factor (FGF), an angiogenic factor, an insulin-like growth factor (IGF), a platelet-derived growth factor (PDGF), an epidermal growth factor (EGF), a vascular endothelial growth factor (VEGF), a nerve growth factor (NGF), a neurotrophin, a bone morphogenetic protein (BMP), osteogenin, osteopontin, osteocalcin, cementum attachment protein, erythropoietin, thrombopoietin, tumor necrosis factor (TNF), an interferon, a colony stimulating factor (CSF), or an interleukin, among others. The bioactive factor may be a BMP, PDGF, FGF, VEGF, TGF, insulin, among others. Examples of BMPs include but are not limited to BMP-2, BMP-3, BMP-4, BMP-5, BMP-6, BMP-7, BMP-8, BMP-9, BMP-10, BMP-11, BMP-12, BMP-13, BMP-14, BMP-15, and a mixture thereof.

In some embodiments, the bioactive factor may include chemokines. Chemokines refers to a family of small proteins secreted from cells that promote the movement or chemotaxis of nearby cells. Some chemokines are considered pro-inflammatory and can be induced during an immune response while others are considered homeostatic. Typically, chemokines exert their chemoattractant function and other functions by binding to one or more chemokine receptors. Chemokines include proteins isolated from natural sources as well as those made synthetically, by recombinant means or by chemical synthesis. Exemplary chemokines include, but are not limited to, MCP-1, Eotaxin, SDF-1ß, GRO-α, MIP-1ß, IL-8, IP-10, MCP-3, MIP-3α, MDC, MIP-1α, BCA-1, GCP-2, ENA-78, PBP, MIG, PF-4, PF-4-var1, SDF-2, MCP-2, MCP-4, MIP-4, MIP-3ß, MIP-2α, MIP-2ß, MIP-5, HCC-1, RANTES, Eotaxin-2, TARC, I-309, Lymphotactin, Lungkine, C10, MIP-1γ, MCP-5, LEC, Exodus-2, MIP-3, TECK, Eotaxin-3, CTACK, MEC, SCM-1ß, I-TAC, BRAK, SR-PSOX, Fractalkine, LD78-ß, MIP-1b2, and others known to those of skill in the art. References to chemokines typically include monomeric forms of such chemokines. Chemokines also include dimeric or other multimeric forms.

In additional embodiments, the bioactive factor may also include small molecules drugs. Small molecule drugs include a molecule, whether naturally-occurring or artificially created (e.g., via chemical synthesis) that has a relatively low molecular weight and that is not a protein, a nucleic acid, or a carbohydrate. In one aspect, though not necessarily, small molecule drugs are monomeric and have a molecular weight of less than about 1500 g/mol. In another aspect, the drug is one that has already been deemed safe and effective for use by the appropriate governmental agency or body. For example, drugs for human use listed by the FDA under 21 C.F.R. §§ 330.5, 331 through 361 and 440 through 460; drugs for veterinary use listed by the FDA under 21 C.F.R. §§ 500 through 589, incorporated herein by reference, are all considered acceptable for use in inventive conjugates. In another aspect, the small molecule drugs may include agonists of a Sphingosine-1-phosphate (SIP) agonist, such as fingolimod (FTY720), which is a synthetic compound that acts as an agonist of the S1P1, S1P3, S1P4, and SIPS receptors when phosphorylated into FTY720P. For example, the small molecule drugs may include the following molecules:

FTY720 (fingolimod)

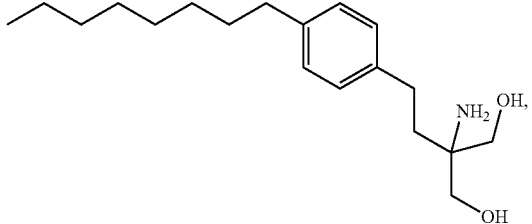

2-amino-2-(4-octylphenethyl)propane-1,3-diol

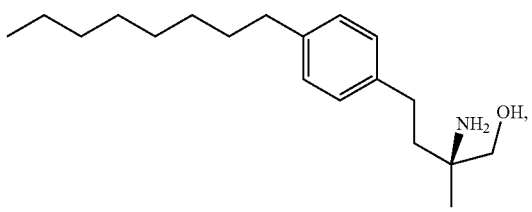

(5')-2-amino-2-methyl-4-(4-octylphenethyl)butan-1-ol

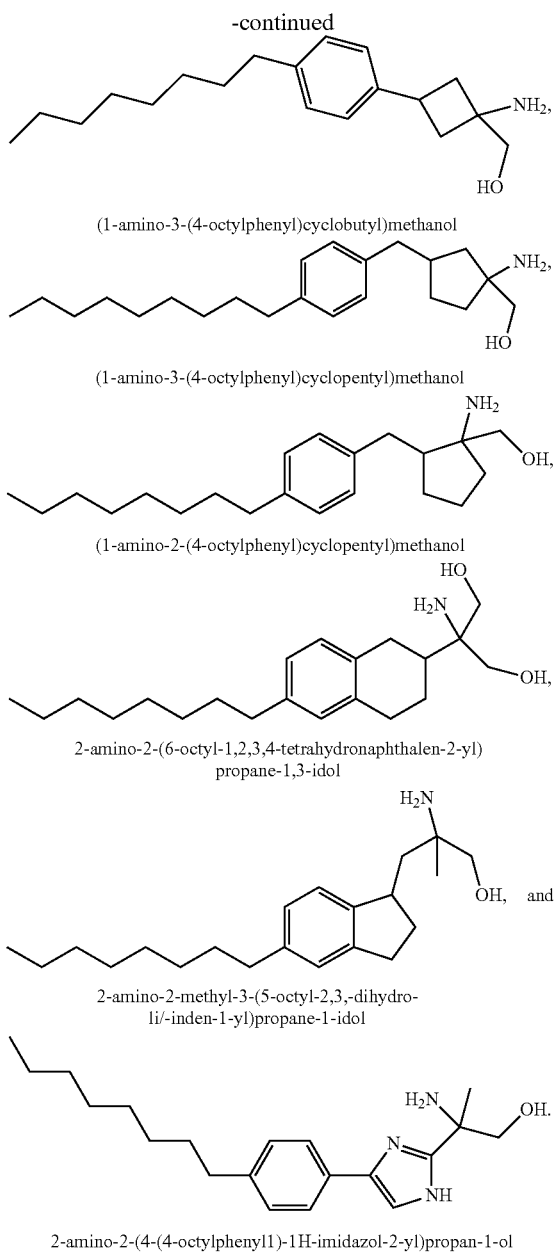

The bone matrix implants may further comprise a tissue, an organ, a biocompatible matrix and/or a mixture of two or more thereof. The bone matrix implants may comprise bone, cartilage, and/or connective tissue.

The invention also relates to methods of preparing a film of bone matrix on a surface. The method of preparing a film of bone matrix on a surface according to some embodiments of the present invention comprises dissolving a bone in an amount of an anhydrous solvent comprising (i) hexafluoroisopropanol (HFP), 2, 2, 2-trifluoroethanol (TFE) or isopropanol, and (ii) at least about 5 wt % trifluoroacetic acid (TFA) sufficient to form a bone matrix solution; exposing the bone matrix solution to conditions sufficient to evaporate an amount of the solvent to form a colloidal gel; coating the surface with the colloidal gel, and exposing the coated surface to conditions sufficient to further evaporate an amount of solvent to form a film. The invention further relates to a synthetic surface coated with the bone matrix produced by the method described herein.

In some embodiments, the film of the bone matrix may be formed on a surface of another biocompatible matrix. In further embodiments, the biocompatible matrix is an implantable biocompatible matrix that can function as a support system for the bone matrix described herein. A biocompatible matrix should be non-toxic, non-eliciting or stimulating severe inflammatory response or immunological rejections, and devoid of other undesired reactions at the implantation site. In one embodiment, the biocompatible matrix is another bone matrix or cartilage or connective tissue.

In some embodiments, the film of the bone matrix may be formed on a surface of biocompatible matrix including, but not limited to, bone graft implants, synthetic bone graft materials in forms of particulates, sheet, or blocks, tendon and/or ligament in bone tunnels, prosthetic implant, for example, for hip, shoulder, knee, or ankle, and trabecular metal. In further embodiments, the bone graft implants may include allograft or xeno-graft. In yet further embodiments, the bone graft implants may include structural bone implants including, but not limited to, monolithic or composite spinal implants (e.g., VERTIGRAFTs from LifeNet Health) and bone struts or blocks. In yet further embodiments, the bone graft implants may include demineralized, or non-demineralized bone particulates, including, but not limited to, cortical, cancellous, or cortical cancellous bone. In other embodiments, the film of the bone matrix may be formed on cell or tissue culture surface.

Suitable biocompatible matrices include, but are not limited to, porous biocompatible scaffolds into which bone cells or progenitor cells may migrate. Osteogenic or chondrogenic cells, i.e., cells involved in the process of deposition of new bone material or cartilagenous material, respectively, can often attach to such porous biocompatible matrices, which can then serve as scaffolding for bone and cartilage tissue growth. Cells involved in the process of deposition of new ligament or tendon material can also attach to such porous biocompatible matrices. For certain applications, the biocompatible matrix should have sufficient mechanical strength to maintain its three dimensional structure and help support the immobilization of the bone segments being united or grafted together. Porous biocompatible matrices which provide scaffolding for tissue growth can accelerate the deposition of new bone or the rate of bone growth and are said to be "osteoconductive." Osteoconductive biocompatible matrices are especially useful in the pharmaceutical compositions described herein. Porous biocompatible matrices which provide scaffolding for tissue growth can accelerate the deposition of new cartilage or the rate of cartilage growth and are said to be "chondroconductive." Osteoconductive biocompatible matrices are especially useful in the pharmaceutical compositions described herein. Chondroconductive biocompatible matrices are especially useful in the pharmaceutical compositions described herein. The osteoinductive or chondroinductive activity of the surface coated with the bone matrix may or may not be altered, including but not limited to, enhanced activity, relative to a surface without the bone matrix coating or a natural surface without any coating. Thus, the osteoconductive or chondroconductive activity of the biocompatible matrices treated with the bone matrix of the present invention may be enhanced compared to matrices not treated with the bone matrix described herein. Of course, the biocompatible matrices are considered to be osteoconductive or chondroconductive if cells within the biocompatible matrix begin to differentiate into more osteoblast-like or chondrocyte-like appearing or functional cells, respectively.

The biocompatible matrices according to some embodiments of the present invention can be derived from natural sources or they can be synthetic or a mixture of both. Biocompatible matrices from natural sources may also comprise natural polymers, including, but not limited to, collagen, hyaluronic acid, alginate, albumin, fibrinogen-fibrin, chitosan, elasin, laminin, connective tissues, intervertebral disc, cortical or cancellous bone, demineralized or mineralized bone, fascia lata, dermis, muscle, ligament, tendon, cartilage including articular/hyaline cartilage, elastic cartilage, and fibrocartilage, a mixture thereof, and mixture of reconstituted tissue. Biocompatible matrices from synthetic sources refer to any material not produced by living organisms, which may include, not limited to, the synthetic material made up of organic components, inorganic components, or a mixture thereof. In some embodiments, a synthetic biocompatible matrix may comprise an organic synthetic polymer, such as poly(lactic-co-glycolic acid), polycaprolactone (PCL), polyglycolic acid (PGA), polylactic acid (PLA), polyhydroxybutyrate (PHB), Poly(ethylene glycol) (PEG), poly(ethylene oxide) (PEO)), and others. In some embodiments, a tissue, an organ, or biocompatible matrix comprising at least one of alginate, chitosan, collagen, gelatin, hyaluronic acid, a fibronectin, an elastin, a laminin, and a proteoglycan may be employed. In certain embodiments, a biocompatible matrix comprising inorganic components, such as hydroxyapatite, calcium sulfate, octacalcium phosphate, calcium phosphate, macroporous calcium metaphosphate ceramic, .beta.-tricalcium phosphate, metal, metal alloy, and others, may be used. A biocompatible matrix used in certain embodiments of the present invention may be prepared by demineralizing, decellularizing or devitalizing a tissue or an organ and cells may be seeded onto the biocompatible matrix.

In some embodiments, the bone matrix described herein may be applied to another biocompatible matrix and may be incubated at conditions permitting the generation of a matrix that is partially or fully coated with the bone matrix. In some embodiments, incubation may be carried out at about 40° C. or lower, or between about 10° C. and about 37° C., or about 20° C. and about 37° C. Incubation may be carried out for between at least about 2 minutes and about 120 minutes, about 3 minutes and about 100 minutes, about 4 minutes and about 80 minutes, about 5 minutes and about 60 minutes, and about 5 minutes and about 30 minutes in certain embodiments. Incubation may be performed under static or dynamic conditions, such as with agitation, shaking, stirring, mixing, horizontal motion, rocking, and others.

In some embodiments of the present invention, a biocompatible matrix may be lyophilized before the bone matrix is applied to the biocompatible matrix. In certain embodiments, the bone matrix may be coated on the biocompatible matrix, and the coated matrix may be subsequently lyophilized. The lyophilized, coated matrix can then be rehydrated before it is used. Further, the cells can be seeded onto the matrix before implantation.

Examples of suitable osteoconductive or chondroconductive biocompatible matrices include but are not limited to, collagen (e.g., bovine dermal collagen), fibrin, calcium phosphate ceramics (e.g., hydroxyapatite and tricalcium phosphate), calcium sulfate, guanidine-extracted allogenic bone and combinations thereof. A number of suitable biocompatible matrices are commercially available, such as Collografe™ (Collagen Corporation), which is a mixture of hydroxyapatite, tricalcium phosphate and fibrillar collagen, and Interpore™ (Interpore International), which is a hydroxyapatite biomatrix formed by the conversion of marine coral calcium carbonate to crystalline hydroxyapatite.

A number of synthetic biodegradable polymers can serve as osteoconductive or chondroconductive biocompatible matrices with sustained release characteristics. Descriptions of these polymers can be found in Behravesh (1999) Clinical Orthopaedics 367, S118 and Lu (2000) Polymeric Delivery Vehicles for Bone Growth Factors in Controlled Drug Delivery: Designing Technologies for the Future, Park and Mrsny eds., American Chemical Society, which is incorporated herein in its entirety. Examples of these polymers include polyα-hydroxy esters such as polylactic acid/polyglycolic acid homopolymers and copolymers, polyphosphazenes (PPHOS), polyanhydrides and poly(propylene fumarates).

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson (1997) Adv. Drug Deliv. Rev. 28:5. The incorporation of PEG into the polymer as a blend to form microparticle matrices allows further alteration of the release profile of the active ingredient (see Cleek (1997) J. Control Release 48, 259). Ceramics such as calcium phosphate and hydroxyapatite can also be incorporated into the formulation to improve mechanical qualities.

In one embodiment, the biocompatible matrices used in the methods of the present invention are other types of bone matrices. For example, the bone matrix prepared by the methods described herein can be coated on another type of bone matrix. As used herein, the other types of the bone matrix may be a biocompatible matrix derived from or including elements of natural bone. In some embodiments, the natural bone is mineralized, partially demineralized, demineralized, cancellous, cortical, or cortical cancellous bone. The bone matrices used herein may or may not include additional synthetic components not typically found in bone tissue. Other embodiments include methods utilizing a biocompatible matrix derived from cartilage, other soft tissues such as the dermis, connective tissue, fascia, small intestine submucosa, serous membrane, pericardium, tendon, ligament, muscle, adipose tissue, myelin, blood vessels, base membrane, amniotic membrane and others. A biocompatible matrix prepared from hyaline cartilage, fibrocartilage or elastic cartilage, may be employed in some embodiments. A biocompatible matrix may be prepared from hyaline cartilage found in the condyle, tibial plateau, femoral head, humeral head, costal cartilage, or fibrocartilage found in intervertebral discs, or elastic cartilage found in the epiglottis or ear. In certain embodiments, a biocompatible matrix derived from natural sources that has been optionally cleaned, disinfected, chemically modified, decellularized, particulated, homogenized, lyophilized, gamma ray irradiated, and/or plasticized may be used. Any of the biocompatible matrices used herein may or may not include additional synthetic components not typically found in such tissue.

In one specific embodiment, the bone or cartilage biocompatible matrices may be demineralized or decellularized, respectively. Examples of demineralized matrices and methods of making are described in U.S. Pat. Nos. 6,189,537 and 6,305,379, which are incorporated herein in its entirety.

The biocompatible matrix, tissue, or organ used in certain embodiments of the present invention may be in the form of a powder, particulates, sheets, fibers, gels, putties, paste, blocks, cylinders, sponges, meshes, films, slices, curls, flakes, or wedges, among others. In certain embodiments of the present invention, the biocompatible matrix, tissue, or organ treated with the bone matrix by the methods described herein may be in the form of a powder, fibers, putty, or a sponge. In further embodiments, the sponge can include, for example, the implant having sponge-like structures disclosed in the co-pending, commonly-assigned patent application PCT/US09/04556 entitled "Composition for a Tissue Repair Implant and Methods of Making the Same" filed on Aug. 7, 2009, which is incorporated herein in its entirety. The treated matrices can be used in any of the methods of the present invention.

The invention also relates to methods of cell culture comprising culturing cells on a cell culture surface coated with the bone matrix produced by the method described herein. As used herein, cell culture refers to the maintenance of cells in an artificial environment, commonly referred to as an in vitro environment. The term cell culture is a generic term and may be used to encompass the cultivation not only of individual cells, but also of tissues, organs, organ systems or whole organisms. The cells used in the culture methods disclosed herein can be any prokaryotic or eukaryotic cell. The cell type used in the culture methods disclosed herein need not be from the same species from which the cell support compositions derive. In addition, the cells may be from an established cell line, or they may be primary cells or genetically engineered cells.

For example, the invention provides for growing and/or culturing cells on a cell culture surface coated with the bone matrix produced by the method described herein. "Growing and/or culturing cells cells on a cell culture surface" includes traditional cell culture methods as well as placing on a surface in any setting, such as in natural or synthetic biocompatible matrices or tissues. The cells may be mammalian, such as but not limited to human, bovine, porcine, murine, ovine, equine, canine, feline and others. In some embodiments, the cells that are cultured on the substrate coated with the bone matrix are stem cells. As used herein, a stem cell is used as it is in the art and means a cell that has the ability to divide and give rise to one daughter cell that may be at least partially differentiated and to another daughter cell that retains the developmental potential of the mother cell. As used herein, stem cells can be adipose derived stem cells, dental pulp stem cells, adult stem cells (ASCs), embryonic stem cells (ESCs), committed progenitor cells, and/or induced pluripotent stem cells (iPSCs). In further embodiments, the bone matrix coated surface can be used in in vitro methods for supporting cell growth and proliferation as well as for increasing osteogenesis, chondrogenesis, or ligament/tendon genesis in the stem cells cultured on the bone matrix coated surface.

In some embodiments, the cells may be mesenchymal stem cells, such as adipose-derived stem cells, embryonic stem cells, progenitor cells, differentiated cells, undifferentiated cells, and/or -pluripotent stem cells. Appropriate cells may also include, but are not limited to cells of the ectodermal lineage, cells of the mesodermal lineage, and cells of the endodermal lineage. Examples of cells of the ectodermal lineage include but are not limited to keratinocytes, osteoblasts, chondrocytes, neurons. Examples of cells of the mesodermal lineage include but are not limited to myoblasts, adipocytes, fibroblasts, endothelial cells, or stromal cells. Examples of cells of the endodermal lineage include but not limited to epithelial cells of the auditory tube, the respiratory tract, such as trachea, bronchi, and alveoli of the lungs, the gastrointestinal tract, the urinary bladder and epithelial cells lining all glands. The cells may also be primary cells derived from tissues or organs. Appropriate cell lines used in the present invention may include but are not limited to mesenchymal cell lines, preosteoblastic cell lines, osteoblastic cell lines, and chondroblastic cell lines. The bone matrix may be coated directly into a tissue, organism or other setting such as a matrix, including, but not limited to, bone matrices.

In some embodiments, the cells may be derived from autologous or allogeneic sources. The cells may be differentiated cells including chondrocytes, osteoblasts, osteoclasts, endothelial cells, epithelial cells, fibroblasts, and periosteal cells. Additionally, the cells may be totipotent, pluripotent, multipotent, progenitor, or adult somatic stem cells. The stem cells may be derived from embryos, placenta, bone marrow, adipose tissue, blood vessel, amniotic fluid, synovial fluid, synovial membrane, pericardium, periosteum, dura, peripheral blood, umbilical blood, menstrual blood, baby teeth, nucleus pulposus, brain, skin, hair follicle, intestinal crypt, neural tissue, muscle. The stem cells may be derived from skeletal muscle, smooth muscle, and cardiac muscle. The stem cells may be derived from genetic reprogramming of mature cells, such as induced pluripotent stem cells (iPSCs). All cells may further be derived from living or recently deceased donors.

Any cell described herewith may be cultured on a cell culture surface coated with the bone matrix produced by the method described herein for between about 15 minutes and about 4 weeks, about 2 hours and about 2 weeks, about 2 hours and about 1 week, about 2 hours and about 72 hours, about 24 hours and about 72 hours, or about 24 hours and about 96 hours, at between about 20° C. and about 40° C. or about 30° C. and about 37° C., in an atmosphere containing between about 1% $CO_2$ and about 10% $CO_2$ or about 4% $CO_2$ and about 6% $CO_2$, in certain embodiments. In some embodiments of the present invention, cells may be cultured in the presence of one or more modified growth factors and (1) a tissue or an organ, (2) a matrix, or (3) a combination thereof. Cells that have been cultured in the presence of one or more modified growth factors in a cell culture medium may subsequently be applied to a matrix, a tissue, an organ or a combination thereof, in certain embodiments.

The invention also relates to methods of promoting osteoinductivity, with the methods comprising culturing cells on a cell culture surface coated with the bone matrix produced by the method described herein. As used herein, "osteoinductivity" can refer to causing cells to differentiate into cells that are more osteoblast-like in phenotype, or the term can refer to increasing the proliferation of osteoblasts, or both. The cells, prior to culture on the bone matrix of the present invention, may be undifferentiated or partially differentiated cells. The cells may be present in culture or in a tissue, organ or portion thereof or in an organism. The osteoinductive activity of the surface coated with the bone matrix may or may not be altered, including but not limited to, enhanced activity, relative to a surface without the bone matrix coating or a natural surface without any coating.

The invention also relates to methods of promoting chondroinductivity, with the methods comprising culturing cells on a cell culture surface coated with the bone matrix produced by the method described herein. As used herein, "chondroinductivity" can refer to causing cells to differentiate into cells that are more chondrocyte-like in phenotype, or the term can refer to increasing the proliferation of chondrocytes, or both. The cells, prior to culture on the bone matrix of the present invention, may be undifferentiated or partially differentiated cells. The cells may be present in culture or in a tissue, organ or portion thereof or in an organism. The chondroinductive activity of the surface coated with the bone matrix may or may not be altered, including but not limited to, enhanced activity, relative to a surface without the bone matrix coating or a natural surface without any coating.

The invention also relates to methods of promoting ligament/tendon differentiation, with the methods comprising culturing cells on a cell culture surface coated with the bone matrix produced by the method described herein. As used herein, "ligament/tendon differentiation" can refer to causing cells to differentiate into cells that are more ligament and/or tendon-like in phenotype, or the term can refer to increasing the proliferation of ligament and/or tendon, or both. The cells, prior to culture on the bone matrix of the present invention, may be undifferentiated or partially differentiated cells. The cells may be present in culture or in a tissue, organ or portion thereof or in an organism. The ligament/tendon differentiation activity of the surface coated with the bone matrix may or may not be altered, including but not limited to, enhanced activity, relative to a surface without the bone matrix coating or a natural surface without any coating.

There are a variety of osteoblast, chondrocyte, ligament/tendon differentiation markers that can be measured to assess osteoinductivity, chondroinductivity, or ligament/tendon differentiation, respectively. For example, cells express alkaline phosphatases during the early stages of differentiation toward osteoblast lineages. Therefore, in vitro alkaline phosphatase assays may be used to evaluate osteoinductivity in cells cultured on the surface coated by the bone matrix by the methods described herein. The ability of the bone matrix prepared by the methods of the present invention to stimulate or induce the alkaline phosphatase expression in an otherwise non-bone forming cells, such as myoblast (C2C12 cells), would indicate that the bone matrix of the present invention has osteoinductive activity. In these assays, cells cultured on a surface not coated by the bone matrix of the present invention and on a natural surface without any coating are used as negative controls to show that the baseline alkaline phosphatase expression on non-bone forming cells. The baseline of the osteoblastic markers in the negative control need not be zero, meaning that the cells in the negative control group may have at least some level of phenotypic marker(s). Accordingly, an "osteoinductive" surface of the present invention would simply cause an increase in the osteoblastic markers in experimental cells over control grown on the bone matrix prepared by the methods described herein. Similarly, chondrocyte markers, including but not limited to type X collagen, type II collagen, Sox 9, Aggrecan. Matrilin-1 and CEP-68, to name a few, can be used to assess chondroinductive potential. Moreover, ligament/tendon markers, including but not limited to scleraxis, can be used to assess ligament/tendon differentiation potential.

Moreover, osteoinductivity, chondroinductivity, and ligament/tendon differentiation may be determined in tissue culture by investigating the ability of the bone matrix prepared by the methods of the present invention to differentiate or induce osteoblast phenotype, chondrocyte phenotype, ligament/tendon cell phenotype in cultured cells, such as primary cells, cell lines, or explants. For example, the cells may display increased production of a marker characteristic of osteoblasts and/or chondrocytes, such as alkaline phosphatase, etc. For example, the osteoinductive, chondroinductive, ligament/tendon differentiation potentials of the surface coated with bone matrix may be more than 0.2, 0.4, 0.6, 0.8, 1, 2, 3, 4, 5, 6, 7, 8, 9 or 10 times greater than those not coated with the bone matrix. In another example, the osteoinductive, chondroinductive, ligament/tendon differentiation potentials of the culture on the bone matrix implant described herein may be more than 10, 20, 30, 40, 50, 60, 70, 80, 90, 100, 500 or even 1000 times greater than those of the unmodified growth factors. Of course, this indicates that lower concentrations of modified growth factor, compared to unmodified growth factor are required to achieve the same effects.

Osteoinductivity, chondroinductivity, ligament/tendon differentiation, for assessing the bone, cartilage, ligament or tendon forming potential induced by the bone matrix of the present invention in a location such as muscle, may also be evaluated using a suitable animal model. For example, intramuscular implantation into a rodent has been used as a model to assess osteoinductive activity of bioactive factors.

The invention also relates to methods of promoting cell attachment, proliferation or maintaining the differentiated state or preventing de-differentiation of osteoblasts, chondrocytes, ligament cells, tendon cells and/or any cell type disclosed herein with the methods comprising culturing the cells on a cell culture surface coated with the bone matrix produced by the method described herein. The proliferative activity of the surface coated with the bone matrix may or may not be altered, including but not limited to, enhanced activity, relative to a surface without the bone matrix coating or a natural surface without any coating.

Mitogenicity may be assessed by investigating cell proliferation induced by the bone matrix prepared by the methods of the present invention using various in vitro assays that measure metabolic activity, such as MTT [3-(4,5-dimethylthiazol-2-yl)-2,5-diphenyltetrazolium bromide] assay, alamarBlue® assay, and others. The alamarBlue® assay uses a non-cytotoxic reduction-oxidation indicator to measure cell metabolic activity, making it a nondestructive assay for assessing the mitogenic activity of the bone solution described herein. Proliferation can also be assessed by measuring DNA quantification, such as by using a PicoGreen™ DNA assay, radioactive labeling of DNA synthesis, such as [$^{3H}$]thymidine labeling or BrdU incorporation. Proliferation can also be assessed via manual cell counting, such as staining cells with trypan blue and counting with a hemacytometer.

The invention also relates to methods of increasing or promoting osteogenesis, chondrogenesis, or ligament/tendon genesis in cells. The methods may comprise culturing the cells on a cell culture surface coated with the bone matrix produced by the method described herein. As used herein, "osteogenesis" is the deposition of new bone material or formation of new bone, including, but not limited to, intramembranous osteogenesis and endochondral osteogenesis. As used herein, "chondrogenesis" is the deposition new cartilage material or formation of new cartilage. As used herein, "ligament/tendon genesis" is the deposition new ligament and/or tendon material or formation of new ligament and/or tendon. The osteogenic, chondrogenic, ligament, or tendon inducing activity of the surface coated with the bone matrix may or may not be altered, including but not limited to, enhanced activity, relative to a surface without the bone matrix coating or a natural surface without any coating. The cells may include cells in any tissue in which bone, cartilage, ligament, or tendon formation is desired, such as, but not limited to, bone, cartilage, ligament, muscle, tendon, etc.

The invention also relates to methods of treating a tissue or organ defect or injury, for example, a musculoskeletal, dental or soft-tissue defect or injury, in an animal comprising administering (1) cells cultured on the surface coated with the bone matrix produced by the methods described herein and/or (2) the bone matrix implant described herein to the tissue or organ defect (e.g. osseous defects, defects in cartilage, ligament, tendon, spinal disk, and tendon insertion site to bone).

The invention further relates to methods of treating a tissue or an organ defect or injury, for example a musculoskeletal, dental or soft-tissue defect, in an animal by applying a biocompatible matrix partially or fully coated with the bone matrix by the methods described herein to the defect, and application to the defect may be accomplished by injecting the coated biocompatible matrix into the defect, inserting the coated biocompatible matrix between tissue or organ, or placing the coated biocompatible matrix on top of the defect. The present invention is also directed to treating a defect or injury in an organ by applying a coated biocompatible matrix to the defect.

In yet another embodiment, cells may be seeded onto a biocompatible matrix coated with the bone matrix prepared by the methods provided herein. The cells seeded on the coated matrix can be any cell, such as but not limited to, osteoblasts, chondrocytes, ligament cells, tendon cells, progenitor cells, and stem cells disclosed herein or otherwise known in the art. The seeded cells may be allowed to proliferate and possibly attach to the matrix. Methods of seeding cells onto matrices, such as collagen matrix coated with the bone matrix prepared by the methods provided herein, are well known in the art.

Any of the methods of the present invention can be performed in virtually any setting, such as an in vivo, ex vivo, in situ or in vitro setting. For example, methods of promoting osteogenesis, chondrogenesis, or tendon/ligament inducing activities in cells may be performed in cell culture, may be performed in seeded cells on matrix, or may be performed in an intact organism. Moreover, any combination of any two or more of any of the embodiments described herein are contemplated.

The invention further relates to bone matrix scaffolds comprising one or more bone matrix nanofibers. In one aspect, the bone matrix scaffold may essentially consist of the bone matrix nanofibers. In another aspect, the bone matrix scaffold may consist of the bone matrix nanofibers. The bone matrix scaffold described herein may be biocompatible. A biocompatible bone matrix scaffold may be non-toxic, non-eliciting or stimulating severe inflammatory response or immunological rejections, and/or devoid of other undesired reactions at the implantation site. The bone matrix nanofiber described herein comprises bone.

The bone matrix scaffold and bone matrix nanofiber of the present invention may comprise type I collagen. In some embodiments, total type I collagen may be present in the bone matrix scaffold and/or bone matrix nanofiber of the present invention in an amount from about 50% to about 95%, from about 60% to about 95%, from about 70% to about 95%, or from about 80% to about 95% by weight in it protein content. In additional embodiments, total type II collagen may be present in the bone matrix scaffold and/or bone matrix nanofiber of the present invention in an amount about 10% or less, about 5% or less, about 3% or less, or about 1% or less by weight in it protein content. In further embodiments, collagen type II may be absent from the bone matrix scaffold and/or bone matrix nanofiber of the present invention. The types of collagen that are present or absent in the composition can be easily assessed using routine methods in the art. Methods of identifying and quantifying type of collagen are well known in the art, as disclosed, for example in Schnaper, H. W. and Kleinman, H. K., Pediatr. Neprol., 7:96-104 (1993), which is incorporated by reference.

In one aspect, the bone matrix nanofiber described herein may have less than about 8 wt %, 7 wt %, 6 wt %, 5 wt %, 4 wt %, or 3 wt % residual calcium. In another aspect, the average residual calcium amount in the bone matrix scaffold described herein may be less than about 8 wt %, 7 wt %, 6 wt %, 5 wt %, 4 wt %, or 3 wt %.

The term nanofiber as used herein means a fiber comprising a diameter of about 1000 nm or less. Relative to the parent bulk material, nano-features can impart many extraordinary properties to macrostructures, including superior mechanical, electrical, optical and magnetic properties, adding surface functionality and yielding high surface area. Matrices of nanofibers of varying diameters may show a range of variable surface properties (e.g. hydrophobicity and hydrophilicity), porosities, and usually superior mechanical properties (e.g. tensile strength, stiffness) relative to the material in other forms.

Nanofibers as matrices recently found applications for orchestrating regeneration and cellular repair processes, whereby the nano-architecture itself provides the specific developmental or morphogenetic cues. Along with proteins, growth factors, and therapeutic agents, nanofibers matrices may influence the cellular response. Further, scaffold fiber alignment plays an important biological role, such that, for example, aligned nanofibers guide cell migration, having been applied to regenerating injured neurons by guiding outgrowth. The matrix of electrospun nanofibers may mimic the natural ECM, including properties such as high porosity and high surface to volume ratios, which facilitate oxygen transport and cell waste removal, assist in cell migration across the implanted scaffold, and make delivery of therapeutic agents possible. In implanted structures for clinical use, nanofiber matrices may have further advantages of improved biocompatibility and reduced friction, and thus reduced irritation, upon delivery and as implanted.

In some embodiments, the nanofiber described herein may have an average diameter of about 1000 nm or less, 900 nm or less, 800 nm or less, 700 nm or less, 600 nm or less, 500 nm or less, 400 nm or less, 300 nm or less, 200 nm or less, 100 nm or less, 50 nm or less, 20 nm or less, or 10 nm or less. In additional embodiments, the total nanofibers in the bone matrix scaffolds described herein may have an average diameter of about 1000 nm or less, 900 nm or less, 800 nm or less, 700 nm or less, 600 nm or less, 500 nm or less, 400 nm or less, 300 nm or less, 200 nm or less, 100 nm or less, 50 nm or less, 20 nm or less, or 10 nm or less.

In one aspect, the bone matrix nanofiber described herein may have a length from about 0.1 cm to about 10 cm, from about 1 cm to about 10 cm, from about 0.1 cm to about 20 cm, from about 1 cm to about 20 cm, from about 10 cm to about 20 cm, from about 0.1 cm to about 30 cm, from about 1 cm to about 30 cm, from about 10 cm to about 30 cm, from about 20 cm to about 30 cm, from about 0.1 cm to about 40 cm, from about 1 cm to about 40 cm, from about 10 cm to about 40 cm, from about 20 cm to about 40 cm, from about 30 cm to about 40 cm, from about 0.1 cm to about 50 cm, from about 1 cm to about 50 cm, from about 10 cm to about 50 cm, from about 20 cm to about 50 cm, from about 30 cm to about 50 cm, from about 40 cm to about 50 cm, 0.1 cm to about 60 cm, from about 1 cm to about 60 cm, from about 10 cm to about 60 cm, from about 20 cm to about 60 cm, from about 30 cm to about 60 cm, or from about 40 cm to about 60 cm. In another aspect the total nanofibers in the bone matrix scaffolds described herein may have an average length from about 0.1 cm to about 10 cm, from about 1 cm to about 10 cm, from about 0.1 cm to about 20 cm, from about 1 cm to about 20 cm, from about 10 cm to about 20 cm, from about 0.1 cm to about 30 cm, from about 1 cm to about 30 cm, from about 10 cm to about 30 cm, from about 20 cm to about 30 cm, from about 0.1 cm to about 40 cm, from about 1 cm to about 40 cm, from about 10 cm to about 40 cm, from about 20 cm to about 40 cm, from about 30 cm to about 40 cm, from about 0.1 cm to about 50 cm, from about 1 cm to about 50 cm, from about 10 cm to about 50 cm, from about 20 cm to about 50 cm, from about 30 cm to about 50 cm, from about 40 cm to about 50 cm, 0.1 cm to about 60 cm, from about 1 cm to about 60 cm, from about 10 cm to about 60 cm, from about 20 cm to about 60 cm, from about 30 cm to about 60 cm, or from about 40 cm to about 60 cm.

In one aspect, the bone matrix scaffold has an average porosity from about 60% to about 70%, from about 60% to about 80%, from about 60% to about 90%, from about 60% to about 95%, from about 70% to about 80%, from about 70% to about 90%, from about 70% to about 95%, from about 80% to about 90%, or from about 80% to about 95%.

In some embodiments, the bone matrix nanofiber described herein may be prepared, for example, by electrospinning, meltblowing, bicomponent spinning, forcespinning, flash-spinning, extrusion, core-sheath electrospinning with or without copolymer, or self-assembly.

Alignment of the bone matrix nanofibers in the bone matrix scaffold may be measured by a fast Fourier transform (FFT) analysis. For example, the FFT analysis may be performed by the methods described in Measuring fiber alignment in electrospun scaffolds: a user's guide to the 2D fast Fourier transform approach, Ayres C E, Jha B S, Meredith H, Bowman J R, Bowlin G L, Henderson S C, Simpson D G. J Biomater Sci Polym Ed. 2008; 19(5):603-21, which is incorporated by reference in its entirety. In some embodiments, FFT result of the bone matrix nanofibers described herein may have adjacent major peaks with about 180Z° apart from each other.

In one aspect, the bone matrix scaffold and/or the bone matrix nanofibers may further comprise an accessory polymer. An "accessory polymer" refers to a polymer that may be added to the bone matrix nanofibers and have any effect on their physical, chemical, and/or biological properties (e.g. tensile strength, hydrophillicity, biocompatibility). For example, the accessory polymer may be selected from the group consisting of polycaprolactone, poly(glycolic acid), poly(lactic acid), polydioxanone, poly (lactide-co-glycolide) copolymers, polyesters polysaccharides, polyhydroxyalkanoates, starch, polylactic acid, cellulose, proteins, agar, silks, alginate, collagen/gelatin, carrageenan, elastin, pectin, resilin, konjac, adhesives, gums, polyamino acids, polysaccharides, soy, zein, wheat gluten, casein, chitin/chitosan, serum albumin, hyaluronic acid, lipids/s urfactants, xanthan, acetoglycerides, waxes, surfactants, dextran, emulsan, gelian, polyphenols, levan, lignin, curd, ian, tannin, polygalactosamine, humic acid, shellac, pullulan, poly-gamma-glutamic acid, elsinan, natural rubber, yeast glucans, and synthetic polymers from natural fats and oils.

In another aspect, the bone matrix scaffold and/or the bone matrix nanofibers may further comprise one or more biodegradable, biocompatible polymers. The biodegradable, biocompatible polymers may include, but is not limited to, ethylene vinyl acetate, polyanhydricles, polyglycolic acid, collagen, polyorthoesters, and polylactic acid. The biodegradable, biocompatible polymers may further include a number of synthetic biodegradable polymers that can serve as osteoconductive or chondroconductive biocompatible matrices with sustained release characteristics. Descriptions of these polymers can be found in Behravesh (1999) Clinical Orthopaedics 367, S118 and Lu (2000) Polymeric Delivery Vehicles for Bone Growth Factors in Controlled Drug Delivery: Designing Technologies for the Future, Park and Mrsny eds., American Chemical Society, which is incorporated herein in its entirety. Examples of these polymers include polya-hydroxy esters such as polylactic acid/polyglycolic acid homopolymers and copolymers, polyphosphazenes (PPHOS), polyanhydrides and poly(propylene fumarates).

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson (1997) Adv. Drug Deliv. Rev. 28:5. The incorporation of PEG into the polymer as a blend to form microparticle matrices allows further alteration of the release profile of the active ingredient (see Cleek (1997) J. Control Release 48, 259). Ceramics such as calcium phosphate and hydroxyapatite can also be incorporated into the formulation to improve mechanical qualities.

In another aspect, the bone matrix scaffold and/or the bone matrix nanofibers may further comprise an extracellular matrix component. For example, the extracellular matrix component may include, but is not limited to, collagen, glycosaminoglycans, osteocalcin, osteonectin, bone sialo protein, osteopontin, or mixtures thereof.

In another aspect, the bone matrix scaffold and/or the bone matrix nanofibers may further comprise a bioactive factor.

In another aspect, the bone matrix scaffold and/or the bone matrix nanofibers may further comprise one or more biocompatible material selected from the group consisting of collagen, polycaprolactone, poly(glycolic acid), poly(lactic acid), polydioxanone, poly (lactide-co-glycolide) copolymers, polyesters polysaccharides, polyhydroxyalka noates, starch, polylactic acid, cellulose, proteins, agar, silks, alginate, collagen, gelatin, carrageenan, elastin, pectin, resilin, konjac, adhesives, various gums, polyamino acids, polysaccharides, soy, zein, wheat gluten, casein, chitin, chitosan, serum albumin, hyaluronic acid, lipids, surfactants, xanthan, acetoglycerides, waxes, dextran, emulsan, gelian, polyphenols, levan, lignin, curd, ian, tannin, polygalactosamine, humic acid, cellulose, shellac, pullulan, poly-gamma-glutamic acid, elsinan, natural rubber, yeast glucans, synthetic polymers from natural fats and oils.

In some embodiments, the bone matrix scaffold of the present invention may further comprise a support. In additional embodiments, the bone matrix nanofibers described herein may be attached to and/or cover the support.

The invention also relates to methods of preparing the bone matrix scaffold. The method of preparing the bone matrix scaffold according to some embodiments of the present invention comprises preparing a bone matrix solution. The method of preparing a bone matrix solution according to some embodiments of the present invention comprises dissolving bone in an anhydrous solvent as described herein.

In one aspect, once the bone matrix solution is prepared, the bone matrix solution may be fabricated into nanofibers and mesh through electrospinning technologies as described in US2010/0120115, which is incorporated by reference. Once fabricated into a scaffold, the bone matrix can be placed into cell culture environment as disclosed herein.

Figure 2:
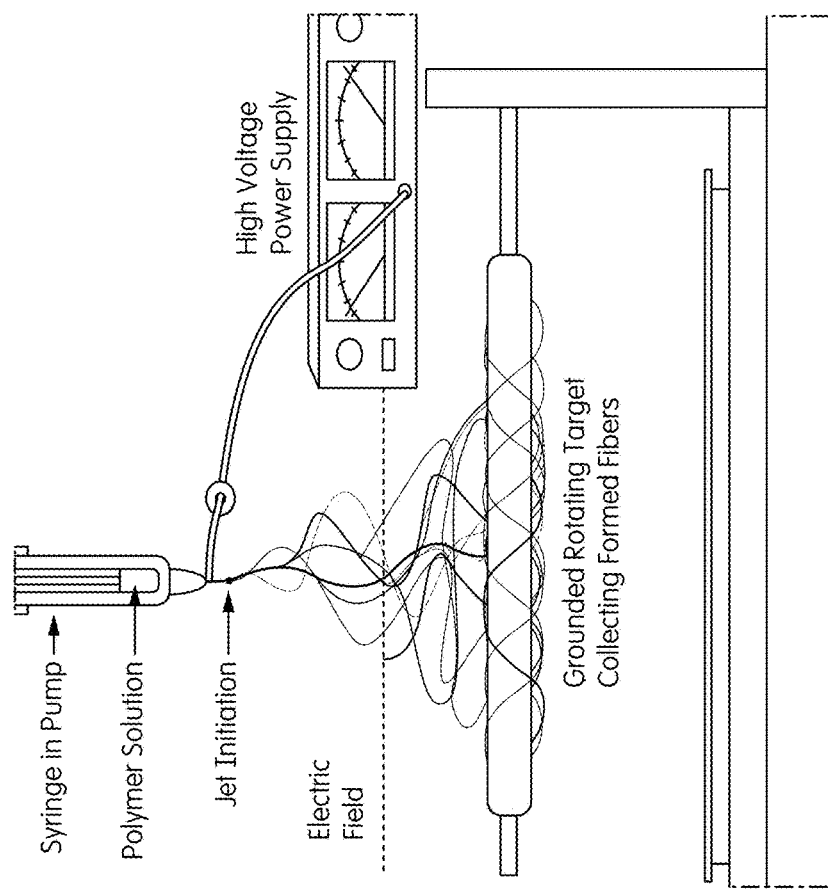
FIG. 2 depicts an exemplary electrospinning apparatus.

In another aspect, the bone matrix solution described herein may be fabricated into nanofibers and mesh using the exemplary electrospinning setup as shown in FIG. 2. Electrospinning typically involves a polymer solution (or melt) maintained at its surface tension on the tip of a nozzle via a syringe in a pump. For example, when sufficiently high voltage is introduced (e.g. 15-40 kV) to the polymer in solution to create a charge imbalance, the solution is drawn towards a grounded collector through the static electric field. As the polymer erupts from the needle and the assembling polymer whip through space, it may be subjected to a series of stretching and bending instabilities, resulting in plastic stretching and elongation to minimize these instabilities generated by repulsive electrostatic forces. As the polymer travels through space and rapidly thins into a fine stream, the solvent may evaporate, and the polymer may assemble into fibers, leaving dry nano- to micro-scale fibers of tailorable physical attributes on the collector.

Additionally, when high electrical potential is applied to a low viscosity polymer melt or solution, electrospraying may occur, which is typified by the polymer jet breaking down into fine droplets. It is therefore possible to produce particles or nano- to micro-sphere particles, fibers and bead-and-string type structures via this process from simply altering the solution or electrospinning apparatus setup variables. Among the variable in electrospinning that can be changed to tailor the final product, such parameters as polymer solution properties, applied electrical potential, polymer molecular weight, polymer solution flow rate, distance between spinner and collector, ambient parameters (humidity, air velocity, temperature) and motion of the collecting target may be altered to form defect-free nanofibers of controlled fiber distribution, diameter and alignment.

In some embodiments, the method of preparing the bone matrix scaffold according to some embodiments of the present invention comprises preparing a bone matrix solution by dissolving bone in an amount of an anhydrous solvent comprising (i) hexafluoroisopropanol (HFP) or 2, 2, 2-trifluoroethanol (TFE) and (ii) at least about 5 wt % trifluoroacetic acid (TFA) sufficient to form a bone matrix solution at a temperature between about 0° C. and about 22° C., and electrospinning the bone matrix solution as described herein to form the bone matrix scaffold.

In one aspect, once the bone matrix solution is prepared, the bone matrix solution may be fabricated into scaffolds through neutralizing the bone matrix solution. For example, the neutralizing the bone matrix solution may comprise titrating sodium hydroxide from the bone matrix solution into a solution. In some embodiments, the neutralization may be performed using a neutralizing solution. The "neutralizing solution" described herein may be an acid-neutralizing solution present in an amount sufficient to raise the pH of the acidic bone matrix solution to about 7.0 to about 7.5 after mixing and/or rinsing. In another aspect, the acid-neutralizing solution may be present in an amount sufficient to raise the pH of the acidic bone matrix solution to about 6.5 to about 7.45 after mixing and/or rinsing. In another aspect, the acid-neutralizing solution may be present in an amount sufficient to raise the pH of the bone matrix solution to about 7.0 to about 7.4 after mixing and/or rinsing. In some embodiments, the acid-neutralizing solution is selected from the group consisting of a bicarbonate solution, a phosphate solution, a carbonate solution, a sodium hydroxide solution, a potassium hydroxide solution, a calcium hydroxide solution, an aluminum hydroxide solution, and any combination of these solutions.

In another aspect, the method of preparing the bone matrix scaffold described herein may further comprise transferring the bone matrix solution into an acid-resistant mold and drying the bone matrix solution. The drying may be performed by, for example, air drying, vacuum drying, heat drying, or freeze drying. In another aspect, the dried bone matrix solution may be neutralized by rinsing it with a neutralizing solution described herein. In another aspect, the method of preparing the bone matrix scaffold described herein may further comprise rinsing the dried bone matrix solution with water. In some embodiments, the bone matrix solution may comprise sodium chloride granulates.

In one aspect, the method of preparing the bone matrix scaffold according to some embodiments of the present invention may further comprise crosslinking the bone matrix solution. In some embodiments, the crosslinking may be performed by any conventional chemical crosslinking method (e.g. chemical reagent-promoted, chemically reactive linker-promoted and/or enzyme-promoted) and/or dehydrothermal crosslinking method (e.g. heat-promoted condensation), forming the covalently crosslinked bone matrix. In additional embodiments, the crosslinking comprises applying a cross-linking agent to the bone matrix solution. For example, the cross-linking agent may be selected from the group consisting of 1-Ethyl-3-(3-dimethylaminopropyl) carbodiimide (EDC), EDC/hyaluronic acid, genipin, and glutaraldehyde.

In another aspect, the method of preparing the bone matrix scaffold according to some embodiments of the present invention may further comprise applying an accessory polymer described herein to the bone matrix solution. In another aspect, the method of preparing the bone matrix scaffold according to some embodiments of the present invention may further comprise adding a bioactive factor described herein to the bone matrix scaffold.

The invention also relates to bone matrix implants produced by the methods of preparing the bone matrix scaffold. An "implant" refers to any object that is designed to be placed partially or wholly within a patient's body for one or more therapeutic or prophylactic purposes such as for tissue augmentation, contouring, restoring physiological function, repairing or restoring tissues damaged by disease or trauma, and/or delivering therapeutic agents to normal, damaged or diseased organs and tissues. A "bone matrix implant" refers to a medical device or implant that includes a volume replacement material for augmentation or reconstruction to replace a whole or part of a bone structure. A predetermined shape of the bone matrix implant may be varied to fit the implant site. A "bone matrix" refers to any mixture of the volume replacement materials for augmentation or reconstruction to replace a whole or part of a bone structure.

The invention also relates to methods of cell culture comprising culturing cells on a bone matrix scaffold produced by the method described herein.

For example, the invention provides for growing and/or culturing cells on a bone matrix scaffold produced by the method described herein. "Growing and/or culturing cells on a bone matrix scaffold" includes traditional cell culture methods as well as placing on a surface in any setting, such as in natural or synthetic biocompatible matrices or tissues. In some embodiments, the cells that are cultured on the bone matrix scaffold are stem cells. In further embodiments, the bone matrix scaffold can be used in in vitro methods for supporting cell growth and proliferation as well as for increasing osteogenesis, chondrogenesis, or ligament/tendon genesis in the stem cells cultured on the bone matrix scaffold.

Any cell described herewith may be cultured on a bone matrix scaffold produced by the method described herein for between about 15 minutes and about 4 weeks, about 2 hours and about 2 weeks, about 2 hours and about 1 week, about 2 hours and about 72 hours, about 24 hours and about 72 hours, or about 24 hours and about 96 hours, at between about 20° C. and about 40° C. or about 30° C. and about 37° C., in an atmosphere containing between about 1% $CO_2$ and about 10% $CO_2$ or about 4% $CO_2$ and about 6% $CO_2$, in certain embodiments.

The invention also relates to methods of promoting osteoinductivity, with the methods comprising culturing cells on a bone matrix scaffold produced by the method described herein. The cells, prior to culture on the bone matrix scaffold of the present invention, may be undifferentiated or partially differentiated cells. The osteoinductive activity of the bone matrix scaffold may or may not be altered, including but not limited to, enhanced activity, relative to other scaffolds without the bone matrix nanofiber described herein.

The invention also relates to methods of promoting chondroinductivity, with the methods comprising culturing cells on a bone matrix scaffold produced by the method described herein. The cells, prior to culture on the bone matrix of the present invention, may be undifferentiated or partially differentiated cells. The chondroinductive activity of the bone matrix scaffold may or may not be altered, including but not limited to, enhanced activity, relative to other scaffolds without the bone matrix nanofiber described herein.

The invention also relates to methods of promoting ligament/tendon differentiation, with the methods comprising culturing cells on a bone matrix scaffold produced by the method described herein. The cells, prior to culture on the bone matrix of the present invention, may be undifferentiated or partially differentiated cells. The ligament/tendon differentiation activity of the bone matrix scaffold may or may not be altered, including but not limited to, enhanced activity, relative to other scaffolds without the bone matrix nanofiber described herein.

In one aspect, in vitro alkaline phosphatase assays may be used to evaluate osteoinductivity in cells cultured on the bone matrix scaffold prepared by the methods described herein. The ability of the bone matrix prepared by the methods of the present invention to stimulate or induce the alkaline phosphatase expression in an otherwise non-bone forming cells, such as myoblast (C2C12 cells), would indicate that the bone matrix of the present invention has osteoinductive activity. In these assays, cells cultured on other scaffolds without the bone matrix nanofiber described herein are used as negative controls to show that the baseline alkaline phosphatase expression on non-bone forming cells. The baseline of the osteoblastic markers in the negative control need not be zero, meaning that the cells in the negative control group may have at least some level of phenotypic marker(s). Accordingly, an "osteoinductive" bone matrix scaffold of the present invention would simply cause an increase in the osteoblastic markers in experimental cells over control grown on the other scaffolds without the bone matrix nanofiber.

Moreover, osteoinductivity, chondroinductivity, and ligament/tendon differentiation may be determined in tissue culture by investigating the ability of the bone matrix prepared by the methods of the present invention to differentiate or induce osteoblast phenotype, chondrocyte phenotype, ligament/tendon cell phenotype in cultured cells, such as primary cells, cell lines, or explants. For example, the cells may display increased production of a marker characteristic of osteoblasts and/or chondrocytes, such as alkaline phosphatase, etc. For example, the osteoinductive, chondroinductive, ligament/tendon differentiation potentials of the bone matrix scaffold having a bone matrix nanofiber described herein may be more than 0.2, 0.4, 0.6, 0.8, 1, 2, 3, 4, 5, 6, 7, 8, 9 or 10 times greater than the scaffolds without the bone matrix nanofiber. In another example, the osteoinductive, chondroinductive, ligament/tendon differentiation potentials of the culture on the bone matrix scaffold and/or implant described herein may be more than 10, 20, 30, 40, 50, 60, 70, 80, 90, 100, 500 or even 1000 times greater than those of the scaffold and/or implant without any bone matrix nanofiber. Of course, this indicates that lower concentrations of modified growth factor, compared to unmodified growth factor are required to achieve the same effects.

Osteoinductivity, chondroinductivity, ligament/tendon differentiation, for assessing the bone, cartilage, ligament or tendon forming potential induced by the bone matrix scaffold of the present invention in a location such as muscle, may also be evaluated using a suitable animal model.

The invention also relates to methods of promoting cell attachment, proliferation or maintaining the differentiated state or preventing de-differentiation of osteoblasts, chondrocytes, ligament cells, tendon cells and/or any cell type disclosed herein with the methods comprising culturing the cells on a bone matrix scaffold produced by the method described herein. The proliferative activity of the bone matrix scaffold may or may not be altered, including but not limited to, enhanced activity, relative to a scaffold without any bone matrix nanofiber.

Mitogenicity may be assessed by investigating cell proliferation induced by the bone matrix prepared by the methods of the present invention using various in vitro assays that measure metabolic activity, such as MTT [3-(4, 5-dimethylthiazol-2-yl)-2,5-diphenyltetrazolium bromide] assay, alamarBlue® assay, and others. The alamarBlue® assay uses a non-cytotoxic reduction-oxidation indicator to measure cell metabolic activity, making it a nondestructive assay for assessing the mitogenic activity of the bone matrix scaffold and/or bone matrix nanofiber described herein.

The invention also relates to methods of increasing or promoting osteogenesis, chondrogenesis, or ligament/tendon genesis in cells. The methods may comprise culturing the cells on a bone matrix scaffold produced by the method described herein. The osteogenic, chondrogenic, ligament, or tendon inducing activity of the bone matrix scaffold may or may not be altered, including but not limited to, enhanced activity, relative to a scaffold without bone matrix nanofiber described herein.

The invention also relates to methods of treating a tissue or organ defect or injury, for example, a musculoskeletal, dental or soft-tissue defect or injury, in an animal comprising administering (1) cells cultured on the bone matrix scaffold produced by the methods described herein and/or (2) the bone matrix implant described herein to the tissue or organ defect (e.g. osseous defects, defects in cartilage, ligament, tendon, spinal disk, and tendon insertion site to bone).

The invention further relates to methods of treating a tissue or an organ defect or injury, for example a musculoskeletal, dental or soft-tissue defect, in an animal by applying a bone matrix scaffold prepared by the methods described herein to the defect, and application to the defect may be accomplished by injecting the bone matrix scaffold into the defect, inserting the bone matrix scaffold between tissue or organ, or placing the bone matrix scaffold on top of the defect. The present invention is also directed to treating a defect or injury in an organ by applying a bone matrix scaffold to the defect.

In yet another embodiment, cells may be seeded onto a bone matrix scaffold prepared by the methods provided herein. The cells seeded on the bone matrix scaffold can be any cell, such as but not limited to, osteoblasts, chondrocytes, ligament cells, tendon cells, progenitor cells, and stem cells disclosed herein or otherwise known in the art. The seeded cells may be allowed to proliferate and possibly attach to the matrix. Methods of seeding cells onto matrices, such as collagen matrix coated with the bone matrix prepared by the methods provided herein, are well known in the art.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents and patent applications referred to in this application are herein incorporated by reference in their entirety.

The following examples are illustrative and are not intended to limit the scope of the invention described herein.

EXAMPLES

Example 1: Dissolving Bone in Various Solvents

Demineralized bone matrix (DBM) was prepared by methods as shown in U.S. Pat. Nos. 6,189,537 and 6,305,379, which are incorporated herein in its entirety. The demineralized bone powder was dissolved at 100 mg/ml in a volatile solvent or mixture of solvents.

Demineralized bone powder was initially dissolved in TFA or from a 5/95, 10/90, 20/80, 50/50 and 100/0 ratio of organic solvents TFA/HFP, respectively, at a starting concentration of 30-150 mg/ml demineralized bone powder, with final ratios set at 20/80 TFA/HFA and 100 mg/ml for all subsequent experiments, apart from solubility assays. The bone was allowed to vigorously stir for 3-4 days at 4° C. up to 21° C. to maintain intact alpha-helical collagen, or at room temp to 37° C. to more rapidly dissolve the DBM with apparent increase in protein denaturation. This resulting brownish liquid was then further assayed for the ability to form a gel or film though evaporation of the volatile organic solvents with or without subsequent addition of water with the suspension placed at either 4° C., room temp, or 37° C., or through neutralizing the acidity of the liquid through strong base addition, such as sodium hydroxide, with or without a buffer system for physiological pH. DBM was found to dissolve in TFA and TFA/HPF at 4° C. after an extended period of stirring, on the order of 14-28+ days.

DBM powder was dissolved in TFA/HFP, TFA/HFP/Water, and TFA/HFP. DBM was dissolved in TFA/HFP, and the solvent subsequently fully evaporated off to leave behind a semisolid colloidal suspension, or gel, or a thin film coating. The protein banding pattern present in this dissolved DBM in cooled TFA/HFP was also observed for reference with intact bands for the alpha chains of collagen prominently seen, indicating that proteins are maintained in structure and composition between the DBM powder (undissolved) and the DBM dissolved in the organic solvent system.

Other systems that were found to dissolve DBM entirely were a combination of TFA with isopropanol, and TFA with 2,2,2-trifluoroethanol (TFE), for which HFP is a precursor molecule. The DBM was dissolved for 2-6 days. While DBM was dissolved in a mixture of trifluoroacetic acid and isopropanol and in trifluoroacetic acid with 2,2,2-trifluoroetanol, but DBM was not dissolved in 2,2,2-trifluoroethanol and hexafluoroisopropanol even after 2 months of mixing.

A longer period on the order of 10-14 days suggested a degradation of collagen and other matrix proteins as seen on SDS gel analysis. SDS gel analysis was performed on various DBM compositions. The results suggest high homology of proteins present between dissolved DBM (20% TFA/80% HFP; 50% TFA/50% HFP) and unprocessed DBM powder. The degradation of the DBM was observed when an equal volume of distilled water is added to the TFA/HFP mix. The results also showed the degradation of the DBM in 100% TFA solution.

Moreover, TFA/HFP/DBM mixture stirred for three days formed a gel from a fully evaporated solution of the dissolved gel re-suspended when placed in water at 37° C., whereas TFA/HFP/DBM solution stirred for 14 days was only able to form a gel at 4 C. when the DBM was likewise evaporated and rehydrated at placed at 4° C., room temp, and 37° C. TFA/HFP/DBM solution stirred over a 2-6 day period was stirred at 16-21° C., as temperatures above room temp, as can be generated by the stirring plate generating and transferring a slight amount of heat, can potentially degrade the intact proteins. The addition of water into the solvent to dissolve the DBM resulted in radical protein degradation.

Example 2: ELISA Study for Growth Factor Detection

Figure 1:
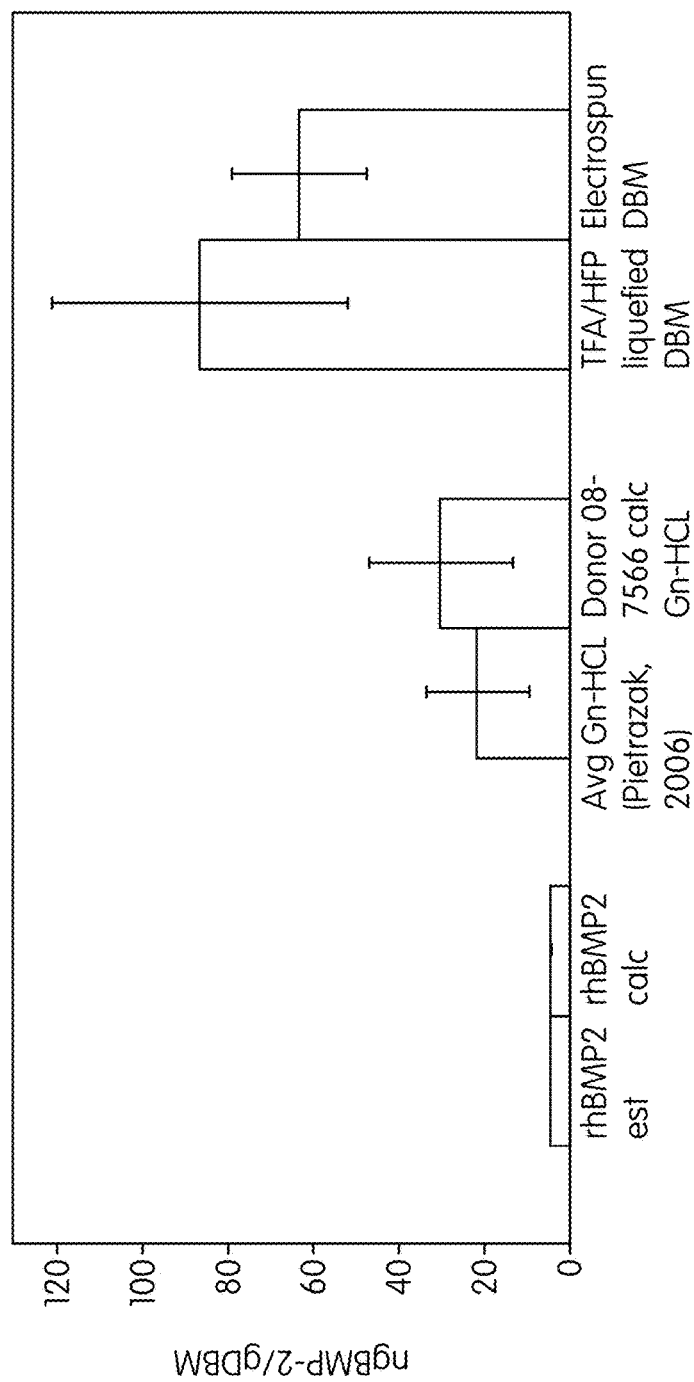
FIG. 1 depicts BMP-2 ELISA assay results. An ELISA for BMP-2 confirms that high quantities of BMP-2 are present in the DBM that was dissolved in TFA/HFP and later slectrospun. An estimated amount of rhBMP2 was added to the assay based on a serial dilution, with the calculated amount by the ELISA confirming the precision of the assay. The average amount of Gn-HCL extracted from DBM by established protocols is shown (purple bar) next to the amount extracted from our tested donor (teal bar) using the established guanidine hydrochloride method. Data was normalized and compared to standard controls, with statistical significance determined by a one-way ANOVE with p<0.05.

An ELISA assay was performed to detect BMP-2 in the dissolved DBM solution (DBM dissolved in TFA/HFP as shown in Example 2), as compared to controls and to the amount of BMP-2 released by the standard BMP-2 isolation technique of guanidine hydrochloride extraction (FIG. 1). The DBM solution prepared as shown in Example 2 was shown to have significantly more BMP-2 released compared to the conventional extraction methods (e.g. Pietrzak et al., J Craniofac Surg., 17, 1, 2006, 84-90) with nearly 4-fold more BMP-2 released per gram of DBM.

Example 3: Preparation of Bone Matrix Scaffolds 1,1,1,3,3,3-hexafluoro-2-propanol (HFP) (CAS#920-66-1) was from Acros Organics (Geel, Belgium), trifluoroacetic acid was obtained from Sigma-Aldrich (T6508, batch #61496MK). Polycaprolactone (PCL) (B6003-1, B6003-2) was from Durect Lactone (Pelham, Ala., http:www.absorbables.com). Bone powder was isolated from human donor bone procured by LifeNet Health, with ECM isolation procedures carried out in the laboratory of Dr. Roy Ogle. The electrospinning apparatus was designed using an Aladdin Programmable Syringe Pump from World Precision Instruments, Inc. (Sarasota, Fla.) and one or two adjustable high voltage power supply from Gamma High Voltage Research (Ormond Beach, Fla.). N-(3-dimethylaminopropyl)-N-ethylcarbodiimide hydrochloride (EDC) and N-hydroxysuccinimide (NHS) was purchased from Thermo Scientific (Pittsburgh, Pa.). Genipin was purchased from Wako (Richmond, Va.).

Demineralized bone powder was dissolved in TFA or a TFA/HFP blend, tested as workable from a 10/90, 20/80, 50/50 and 100/0 ratio of organic solvents, respectively, at 30-150 mg/ml bone powder concentrations, with final ideal parameters set at 20/80 TFA/HFP at 100 mg/ml and used for the subsequent experiments. DBM was also co-electrospun with an equal volume of polycaprolactone (PCL) that was dissolved in HPF at 100 mg/ml. The bone is allowed to vigorously stir for 3-4 days at below room temp (<~21° C.). This resulting brown colored solution was then loaded into the glass syringe with an 18 ga stainless steel needle and secured into the syringe pump, in the device design shown in FIG. 2. A stainless steel plate coated with aluminum foil or number 1 glass coverslips on top of the collector plate were used to collect randomly aligned nanofibers, or the fibers were collected between earthed stainless steel posts 3-10 mm apart to impart fiber alignment, with the stainless steel posts either statically mounted or rotating at around 4,000 RPMs to enhance alignment and maximal thickness of the scaffold. The voltage source was used to apply a +20 kV DC voltage to the positive lead, attached to the metal syringe needle, with the collector either earthed or with a 15 kV DC voltage applied from a second power supply set to opposite polarity. The programmable syringe pump was set to dispense the solution at 0.50-3.50 mL/hr, ideally at 2.5 ml/hr for pure DBM and 4 ml/hr for DBM/PCL mixtures. After approximately 1 hour of electrospinning, the collector was replaced with a new aluminum sheet and the flow rate was changed. Concentrations of 10%, 50%, 90% and 100% demineralized bone blended with PCL were examined, as well as flow rates of 0.5 mL/hr-5.75 mL/hr to identify the ideal parameters (which can be affected day-to-day by relative humidity, ambient temperature, etc.). Further modifications to this arrangement have been made based on intended use, including multiple spinnerets, rotating targets of various shapes and sizes, focusing of the polymer jet by electrode modifications, and additional power source and grounding schemas.

Electrospun demineralized bone matrix and DBM/PCL blended samples were taken from each collector and mounted on aluminum stubs using carbon stickers. The samples were then coated with gold at about 50 nm thickness using a sputter coater. Coated samples were imaged using a JOEL 6400 Scanning electron microscope (SEM) with Orion image processing. Representative images can be seen in FIG. 3.

Figure 3:
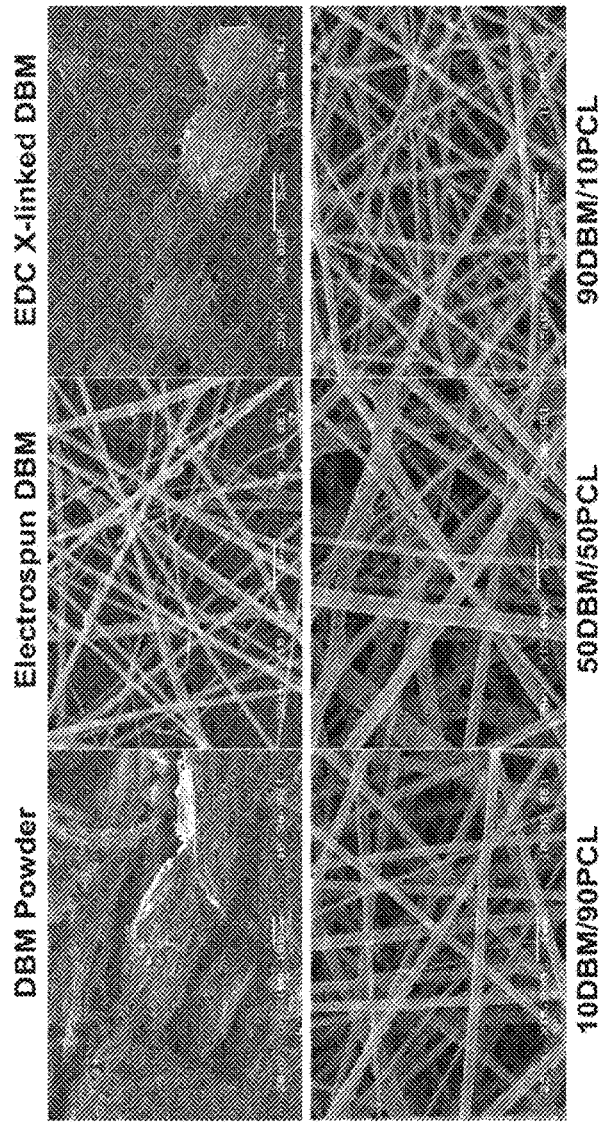
FIG. 3 depicts electrospun bone nano-features. Representative scanning electron micrographs of electrospun demineralized bone matrix. The architecture of the large demineralized bone matrix chips are shown relative to the pure electrospun demineralized bone matrix (note scale bar size differences), both as uncross-linked and as cross-linked with 1-Ethyl-3-(3-dimethylaminopropyl)carbodiimide (EDC), and as blended with various ratios of DBM/PCL.
Figure 4:
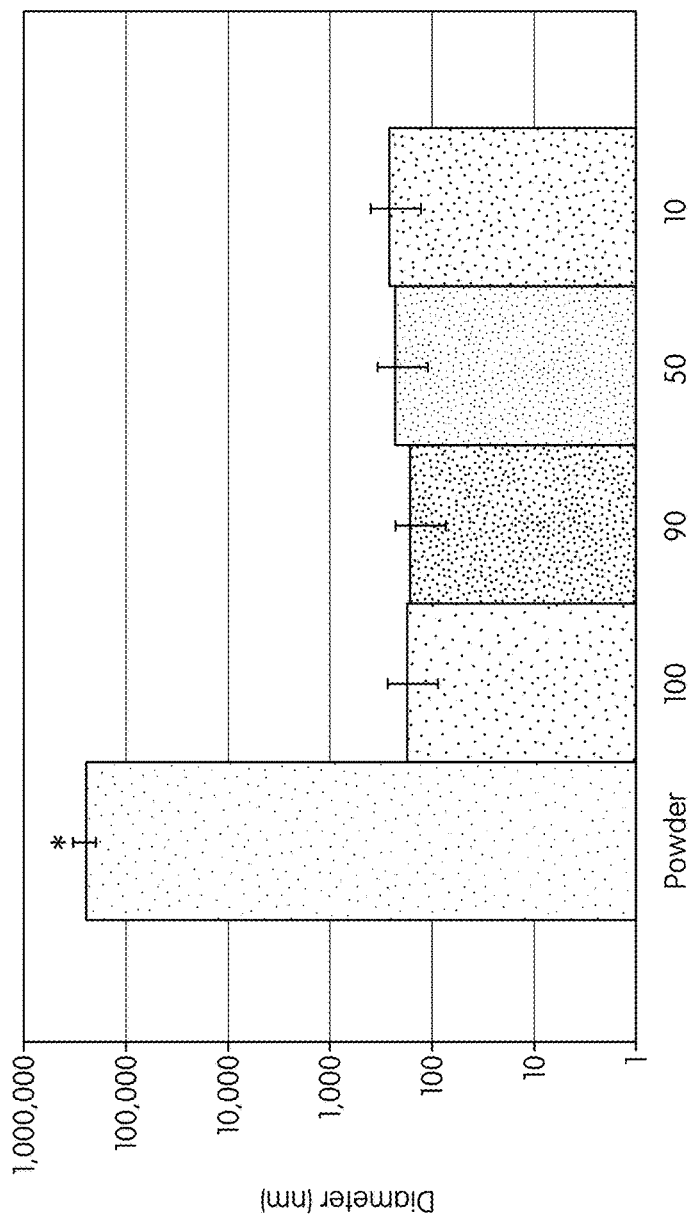
FIG. 4 depicts average electrospun bone matrix fiber size. This graph depicts demineralized bone matrix diameter from raw powder and electrospun nanofibers, with variable amounts of polycaprolactone added to the liquefied bone for electrospinning. "Powder" indicates raw ground bone measured across the particle width. The amount of demineralized bone in electrospun fibers are shown as a percent of DBM relative to the amount of PCL in the copolymer blend as a percentage (100=100% DBM, 10=10% DBM and 90% PCL, etc.). Error bars indicate standard deviation and significance is denoted as *p<0.05, as determined by a one way ANOVA followed by Tukey's test for pairwise comparisons. Note: log scale is used on the ordinate axis.

Scaffolds of pure demineralized bone nanofibers were found to dissolve when placed in aqueous solutions, including culture media, PBS and milliQ water, so 10 mm scaffold punches were tested for stability after crosslinking with various chemical agents under a wide array of conditions. A solution of 0.01% genipin dissolved in ethanol at 37° C. for 24-48 hrs was found to be a suitable cross-linker, maintaining scaffold stability in aqueous solution. A 50 molar excess of EDC with 18 hrs of cross-linking time was also found to sufficiently cross-link demineralized bone scaffold. Additionally, glutaraldehyde vapors also provided stability by lightly cross-linking the electrospun DBM nanofiber scaffold. These so called "zero length cross-linkers" altered the fibrous morphology of the electrospun scaffolds as shown in FIG. 3, however, linkers or spacers commonly used with these cross-linkers will retain the native porous topology of the scaffolds. The average size of the electrospun fibers generated from pure demineralized bone matrix, and as blended with PCL, and as compared to the native demineralized bone power size was calculated by measuring 50 unique points in ImageJ64 (NIH shareware), with results shown in FIG. 4.

Figure 5:
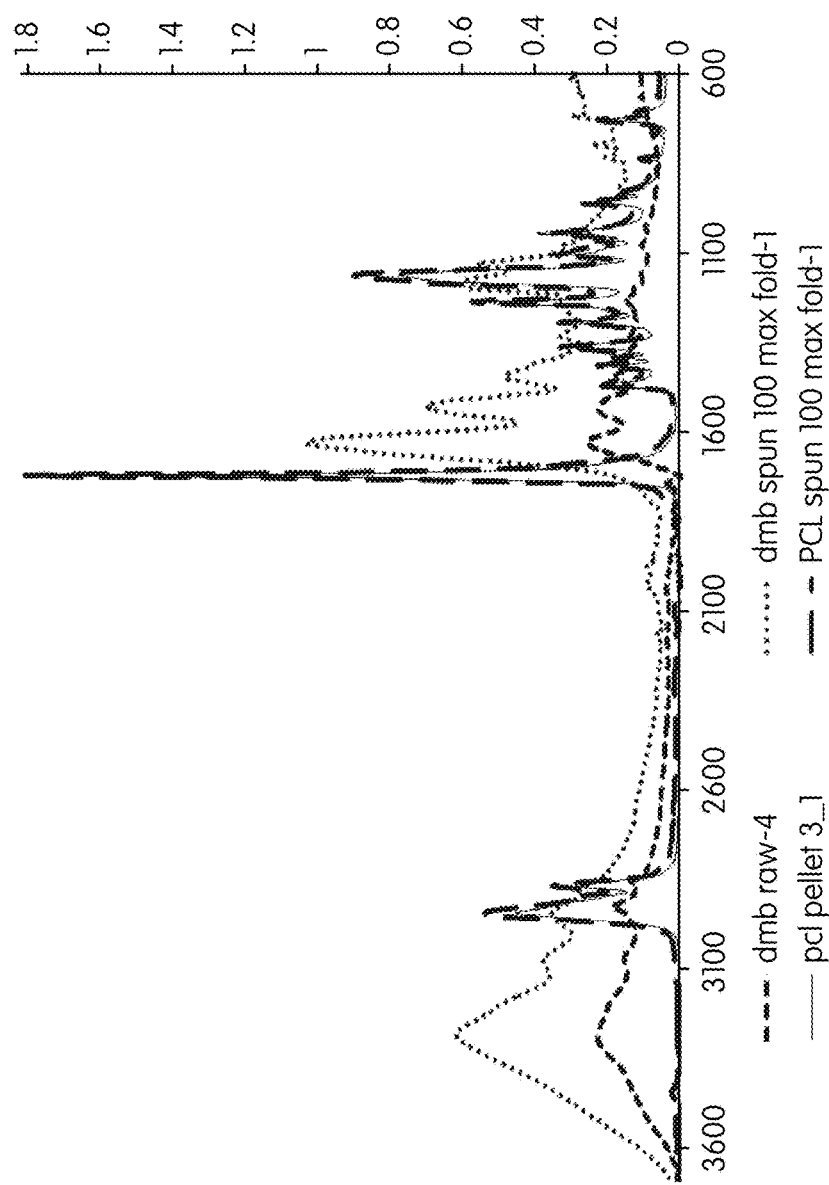
FIG. 5 depicts Fourier Transform Infrared Spectroscopy (FTIR). FTIR analysis of demineralized bone matrix and PCL co-polymer blends was performed, confirming homology of electrospun DMB nanofibers to its native DMB powder form. The peaks noted by red arrows have been shown to associate with an intact alpha-helical structure as present in type I collagen.
Figure 6:
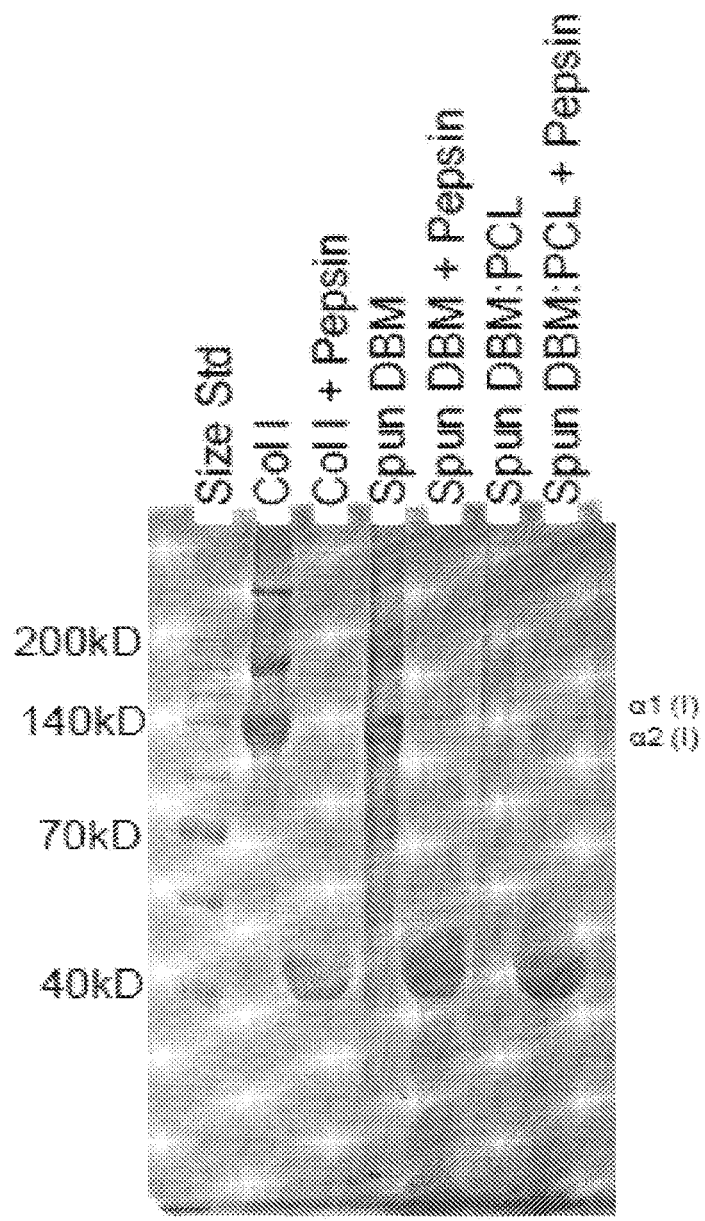
FIG. 6 depicts collagen structural analysis of electrospun demineralized bone. SDS gel show the band pattern of DBM as electrospun alone or with PCL, as compared with pure type I collagen, either with or without pepsin treatment. Size markers (red bands labeled), collagen type I an electrospun DMB are show before and after treatment with pepsin, with the collagen alpha 1 and alpha 2 helices (noted) shown unchanged under the electrospinning conditions.
Figure 7:
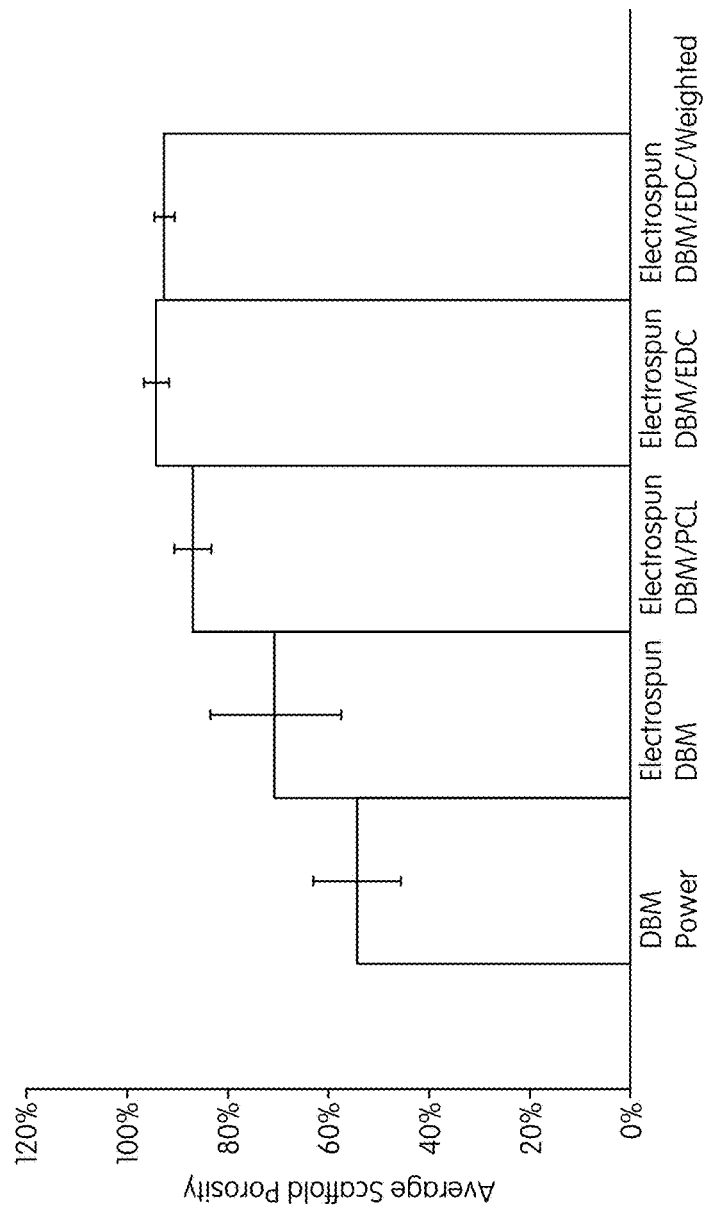
FIG. 7 depicts porosity of electrospun bone matrix scaffolds. The average scaffold porosity was determined by calculating void fraction of dry materials relative to wet material with respect to material density as shown. We show the average scaffold porosity of electrospun DBM in its native/uncrosslinked form, or as cross-linked by blending with either PCL or EDC, or as cross-linked with EDC with the scaffold weighted to prevent material shrinkage. Overall, electrospun DBMs had average porosity above that of demineralized bone matrix powder.

To confirm co-polymerization of demineralized bone and PCL in the forming blended nanofibers of the two materials, FTIR analysis was used to assess the chemical bond structure and to quantitatively determine the presence of each polymer in the different blends. FTIR also was used to show a high degree of similarity between the unprocessed demineralized bone powder and the electrospun nanofibrous mesh as shown in FIG. 5, where peaks/bonds were highly conserved between raw and electrospun DBM, including putative peaks that suggest a maintained alpha helical structure in the collagen present. Lastly, to assess the structure of collagen to be unchanged from the native DBM powder state we compared native DBM and electrospun DBM with pure collagen type I that was either treated or not treated overnight with pepsin to show the maintenance of the alpha 1 and alpha 2 bands of collagen type 1 between samples (FIG. 6). The porosity of the electrospun scaffolds was characterized as shown in FIG. 7.

Example 4: Cell Culture on Bone Matrix Scaffolds

Figure 8:
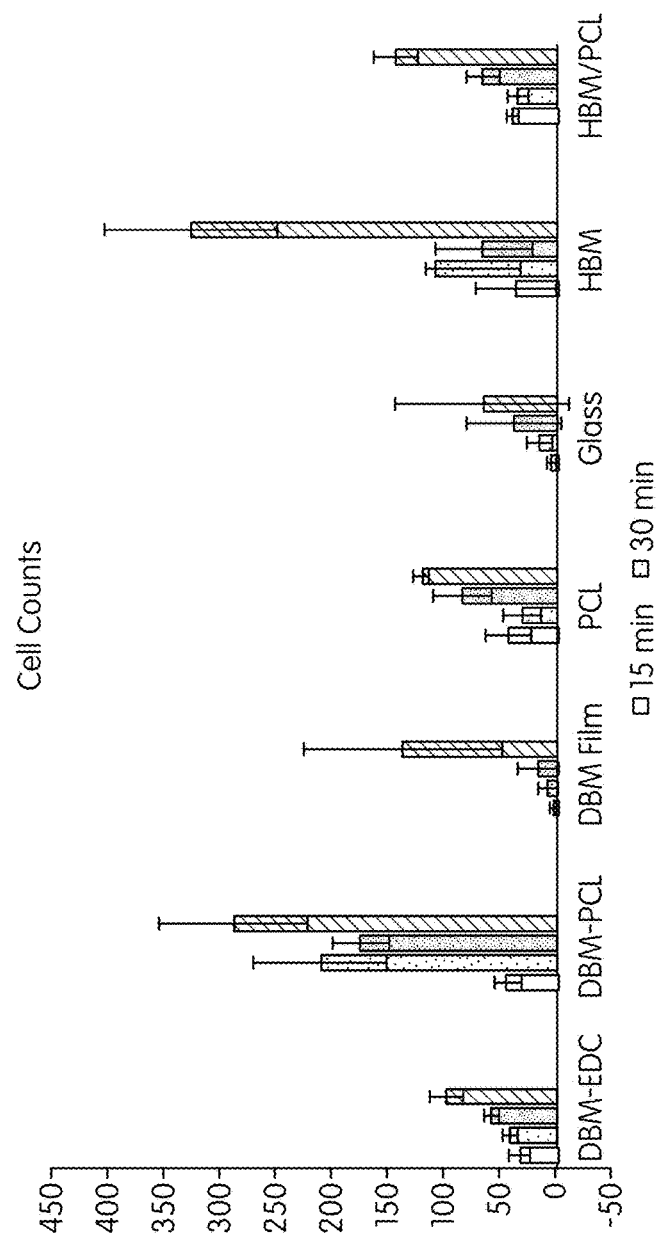
FIG. 8 depicts mesenchymal stem cell attachment on bone matrix scaffolds.

Excellent and rapid mesenchymal stem cell attachment was also demonstrated on electrospun DBM as cross-linked with EDC or blended with PCL as compared to controls are also shown FIG. 8.

Example 5: In Vivo Study

Animal studies with implanted EDC cross-linked DBM and DBM/PCL indicated new bone formation along with high cellularity in electrospun DBM-EDC cross-linked samples with a mild inflammatory response at 4 weeks of gestation of 0.1 cc of material in a rat pouch assay (FIG. 9).

Example 6: Cell Differentiation on Bone Matrix Scaffolds

Alizarin Red S histological stains of electrospun DBM/PCL, PCL and DBM indicated that trace calcium in the native DBM remains present in the electrospun variants of DBM and DBM/PCL (FIG. 10), with the trace calcium believed critical for new bone formation. Toluidine blue histology, along with apparent bone nodule formation, confirmed osteoblastogenesis on samples of electrospun DBM that was dissolved in contact with stem cells grown on plastic (FIG. 10).

The osteoinductive capacity of the electrospun DBM was further confirmed through showing adipose derived stem cells (ASCs) and dental pulp stem cells (DPSCs) were induced to osteoblasts from their contact with the electrospun DBM. Osteoblastogenesis was confirmed using fluorescent microscopy to visualize expression of bone sialo protein I (aka osteopontin) and bone sialo protein II using the respective monoclonal antibodies conjugated to alexa-488 secondary antibodies, with a DAPI stain for the nucleus (FIG. 11) all seen in cells on DBM scaffolds only. The alexa488 fluorescence was absent in control samples and on no-secondary-antibody controls.

What is claimed:
1. A synthetic surface partly or wholly coated with a bone matrix, said matrix comprising a solution of bone in an anhydrous solvent, said solvent comprising (i) hexafluor- oisopropanol (HFP) or 2,2,2-trifluoroethanol (TFE) and (ii) trifluoroacetic acid (TFA), said matrix being in the form of a colloidal gel.

2. An implant comprising the synthetic surface of claim 1.

3. The synthetic surface of claim 1, wherein the bone comprises demineralized bone matrix.

4. The synthetic surface of claim 1, wherein the bone comprises collagen Type I, wherein more than 60% of the collagen Type I is in its native structure.

5. A method of making a synthetic surface, comprising the steps of:
   a) preparing a bone matrix solution by dissolving bone in an amount of an anhydrous solvent comprising (i) hexafluoroisopropanol (HFP) or 2, 2, 2-trifluoroethanol (TFE) and (ii) trifluoroacetic acid (TFA) sufficient to form the bone matrix solution at a temperature lower than about 25° C.;
   b) exposing the bone matrix solution to conditions sufficient to evaporate a portion of the solvent to form a colloidal gel;
   c) coating a synthetic surface with the colloidal gel; and
   d) exposing the coated surface to conditions sufficient to further evaporate an amount of solvent.

6. The method of claim 5, wherein the dissolved bone comprises demineralized bone matrix.

7. The method of claim 5, wherein the dissolved bone comprises collagen Type I, wherein more than 60% of the collagen Type I is in its native structure.

* * * * *